(12) United States Patent
Ishihara et al.

(10) Patent No.: US 10,039,514 B2
(45) Date of Patent: Aug. 7, 2018

(54) COMPUTER READABLE STORAGE MEDIUM, APPARATUS, AND METHOD FOR IMAGE PROCESSING

(71) Applicant: FUJITSU LIMITED, Kawasaki-shi, Kanagawa (JP)

(72) Inventors: Masaki Ishihara, Kawasaki (JP); Takayuki Baba, Kawasaki (JP); Yusuke Uehara, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 57 days.

(21) Appl. No.: 15/215,049

(22) Filed: Jul. 20, 2016

(65) Prior Publication Data

US 2017/0024884 A1  Jan. 26, 2017

(30) Foreign Application Priority Data

Jul. 24, 2015 (JP) ................. 2015-147040

(51) Int. Cl.
| | | |
|---|---|---|
| *G06K 9/00* | (2006.01) | |
| *A61B 6/00* | (2006.01) | |
| *A61B 6/03* | (2006.01) | |
| *G06T 7/00* | (2017.01) | |

(52) U.S. Cl.
CPC ............ *A61B 6/5217* (2013.01); *A61B 6/032* (2013.01); *A61B 6/461* (2013.01); *A61B 6/50* (2013.01);
(Continued)

(58) Field of Classification Search
CPC ........... A61B 5/055; A61B 5/08; A61B 5/085; A61B 5/087; A61B 5/091; A61B 5/1128; A61B 5/742; A61B 6/03; A61B 6/032; A61B 6/461; A61B 6/469; A61B 6/481; A61B 6/486; A61B 6/504; A61B 6/5217; A61B 6/5235; A61B 7/003; A61B 2017/00809; A61B 2018/00541; G06T 7/0012; G06T 7/0014; G06T 7/0016; G06T 7/38; G06T 11/003; G06T 15/08; G06T 2207/10016; G06T 2207/10072–2207/10108; G06T 2207/30061; G06T 2207/30064; G06T 2207/30101; G06T 2207/30172;
(Continued)

(56) References Cited

U.S. PATENT DOCUMENTS

| 7,072,501 B2 * | 7/2006 | Wood ..................... A61B 6/032 |
| | | 382/132 |
| 7,286,694 B2 * | 10/2007 | Oosawa ................. G06T 7/0012 |
| | | 378/20 |

(Continued)

FOREIGN PATENT DOCUMENTS

| JP | 8-103439 | 4/1996 |
| JP | 2004-283373 | 10/2004 |
| JP | 2013-141603 | 7/2013 |

*Primary Examiner* — Jose Couso
(74) *Attorney, Agent, or Firm* — Fujitsu Patent Center

(57) ABSTRACT

A non-transitory computer readable storage medium that stores a program for image processing that causes a computer to execute a process including: detecting a change in a lung based on a plurality of images of the chest scanned at different times, the change in the lung indicating that each position of each part of the lung changes toward a specified position of the lung, and outputting the change of the lung.

8 Claims, 27 Drawing Sheets

(52) U.S. Cl.
CPC .. *G06T 7/0016* (2013.01); *G06T 2207/10076* (2013.01); *G06T 2207/10081* (2013.01); *G06T 2207/30064* (2013.01); *G06T 2207/30096* (2013.01)

(58) Field of Classification Search
CPC . G06T 2207/30004; G06T 2207/30096; G06T 2210/41; G06T 2211/40; G06K 2017/009; G06K 2209/05; G06F 19/30; G06F 19/34; Y10S 378/901; Y10S 128/03; Y10S 128/92; Y10S 706/924; A61M 2210/1039
See application file for complete search history.

(56) References Cited

U.S. PATENT DOCUMENTS

| | | | |
|---|---|---|---|
| 8,655,040 B2* | 2/2014 | Leung | G06T 7/0012 378/8 |
| 8,666,139 B2* | 3/2014 | Zhang | A61B 5/08 382/131 |
| 8,798,343 B2* | 8/2014 | Kabus | A61B 6/5235 378/65 |
| 9,025,849 B2* | 5/2015 | Fouras | H04N 13/0203 382/132 |
| 9,036,887 B2* | 5/2015 | Fouras | A61B 5/08 382/132 |
| 9,370,334 B2* | 6/2016 | Fouras | A61B 5/08 |
| 2004/0249270 A1 | 12/2004 | Kondo et al. | |
| 2013/0182925 A1 | 7/2013 | Razeto et al. | |
| 2013/0194266 A1* | 8/2013 | Forster | A61B 6/5229 345/424 |
| 2015/0150482 A1* | 6/2015 | Fouras | A61B 5/1128 600/410 |
| 2016/0354269 A1* | 12/2016 | Fouras | A61B 5/1128 |
| 2017/0303820 A1* | 10/2017 | Charles | A61B 5/055 |
| 2017/0309026 A1* | 10/2017 | Sakamoto | G06T 7/0016 |
| 2018/0055414 A1* | 3/2018 | Bieri | A61B 5/091 |

\* cited by examiner

FIG. 5

| PATIENT ID : xxx | | |
|---|---|---|
| SERIES DATE | 2014.2.5 | 2014.8.3 |
| BODY PART EXAMINED | CHEST | CHEST |
| SERIES NAME | SERIES A | SERIES B |
| IMAGE LIST | ImageA001<br>ImageA002<br>ImageA003<br>⋮<br>ImageA015<br>ImageA016<br>ImageA017<br>ImageA018<br>⋮<br>ImageA030 | ImageB001<br>ImageB002<br>ImageB003<br>⋮<br>ImageB015<br>ImageB016<br>ImageB017<br>ImageB018<br>⋮<br>ImageB030 |

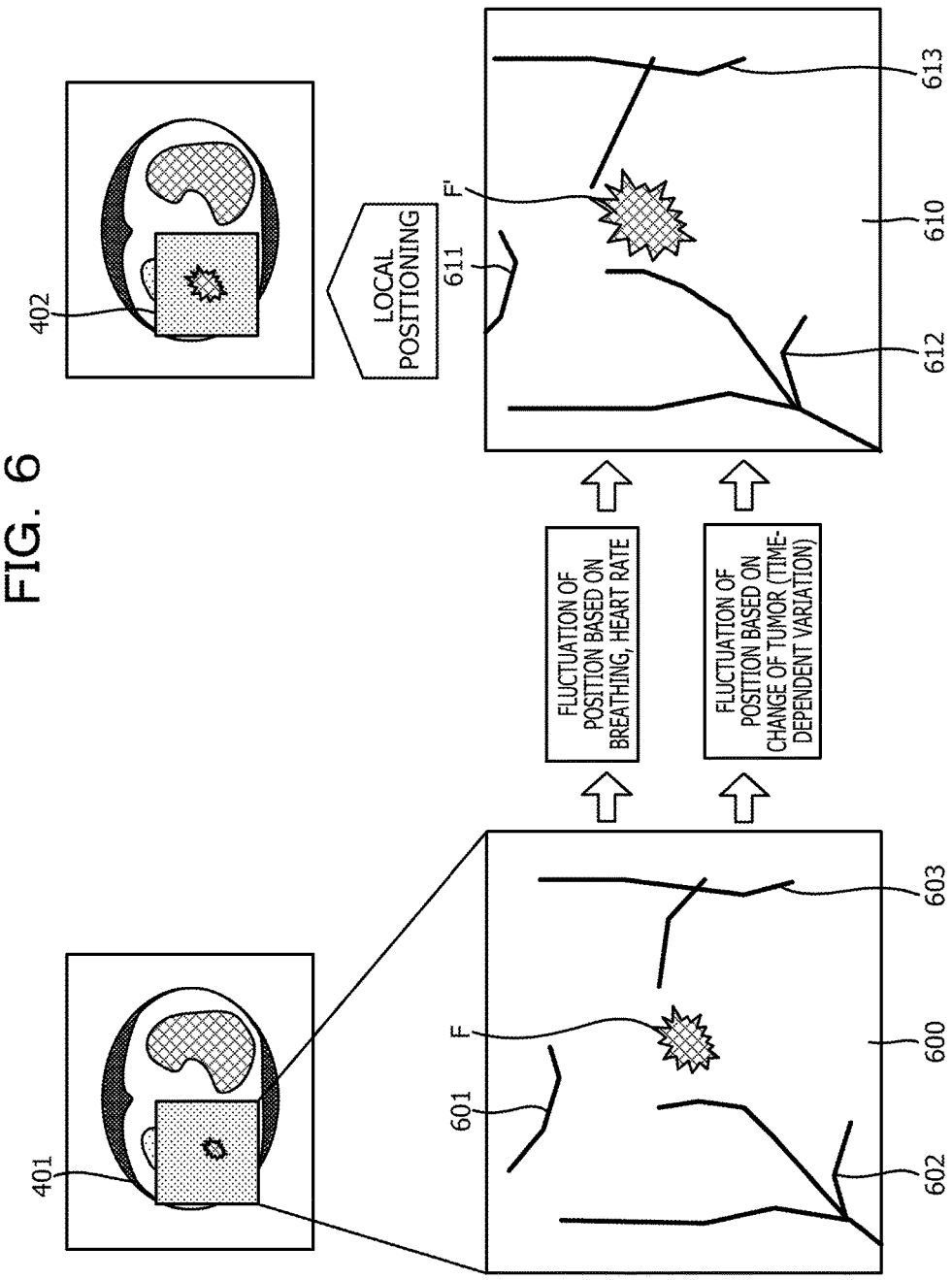

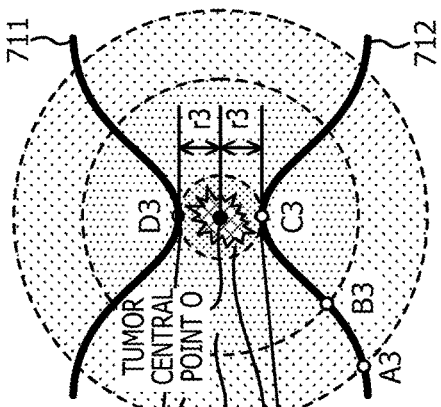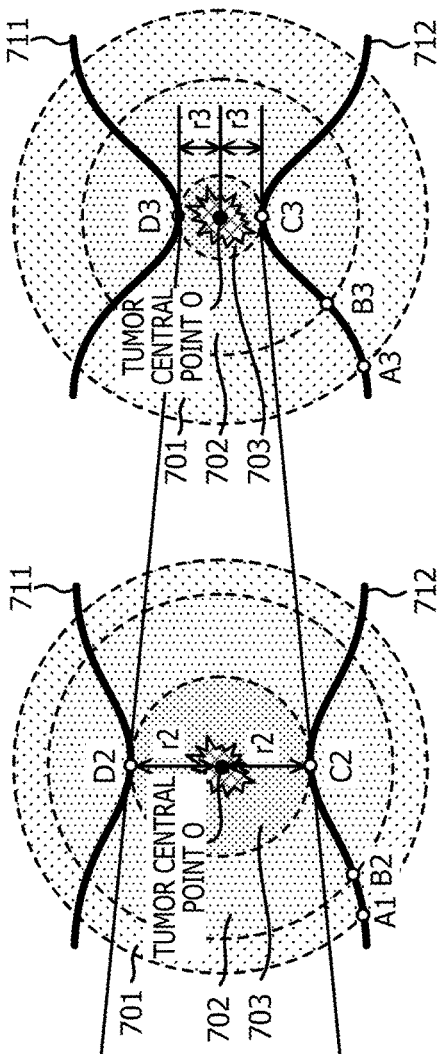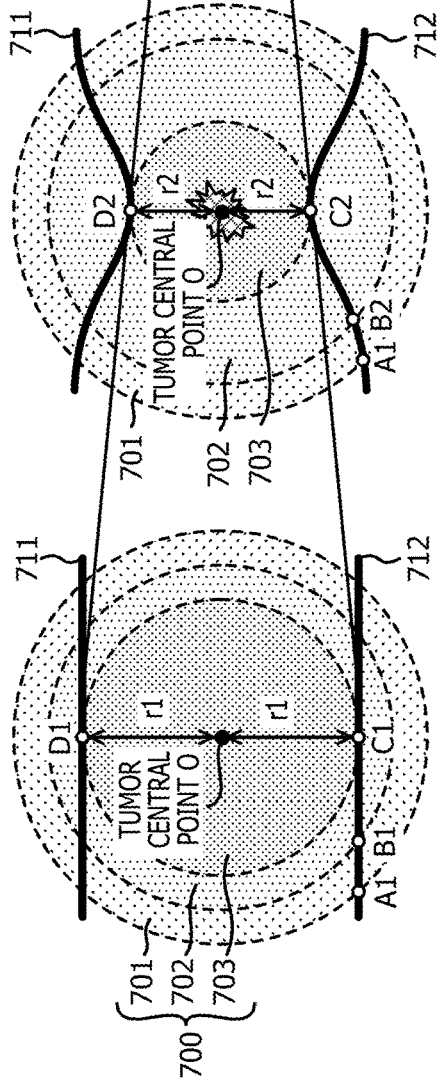

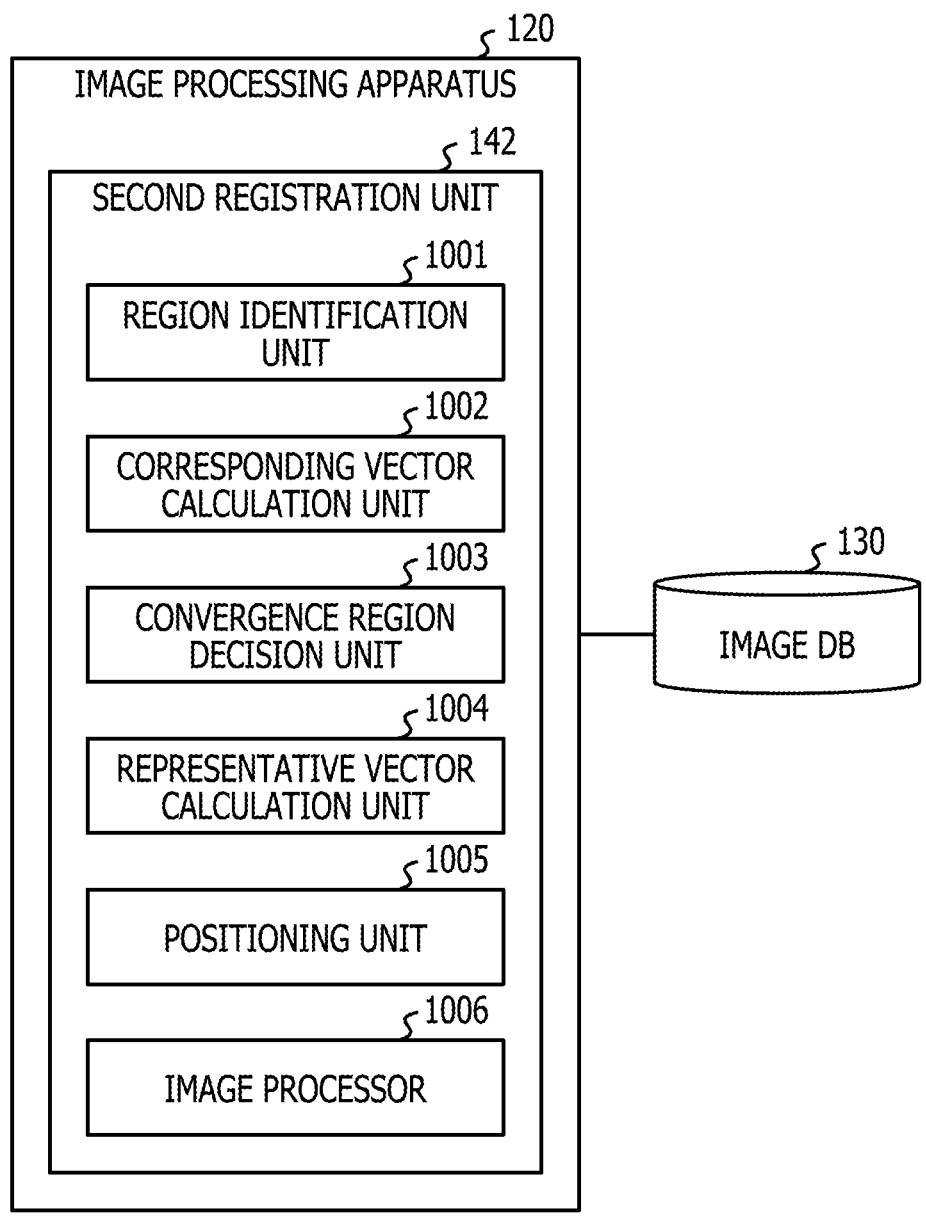

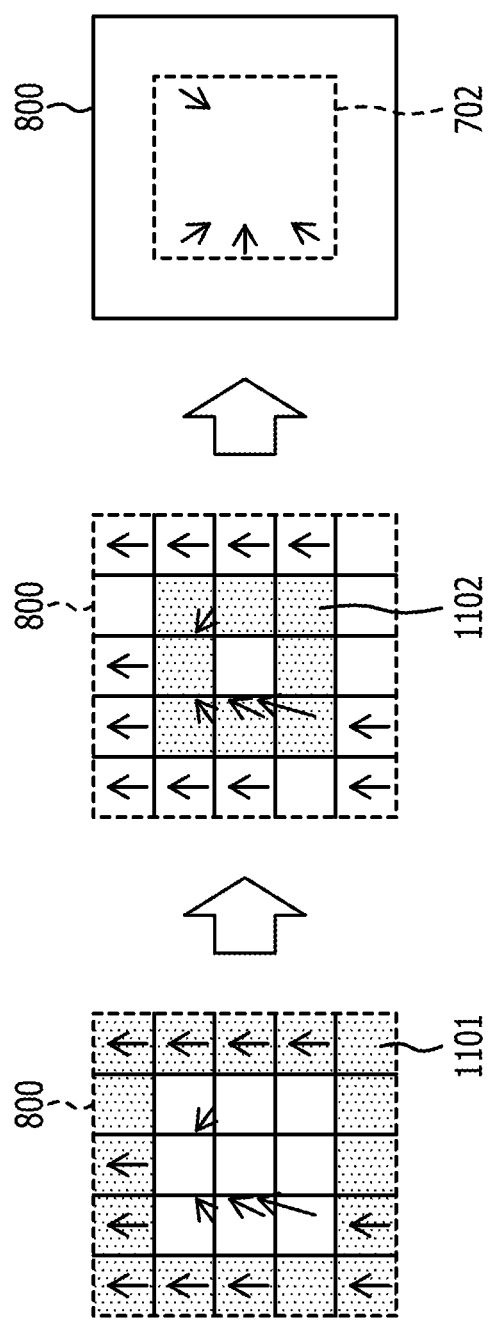

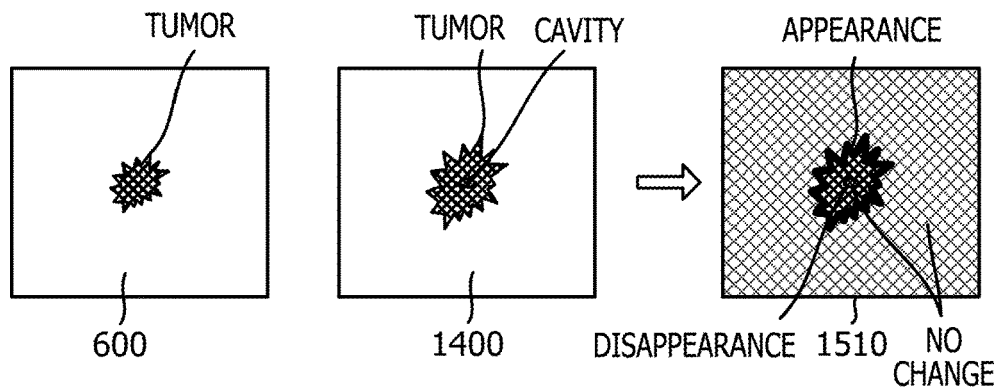
FIG. 15A
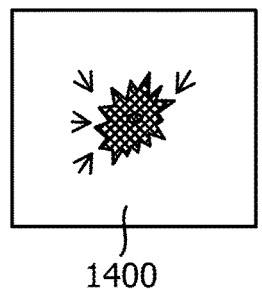
FIG. 15B-1
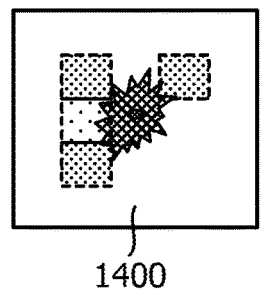
FIG. 15B-2
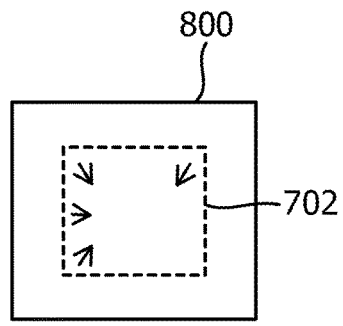
FIG. 15C-1
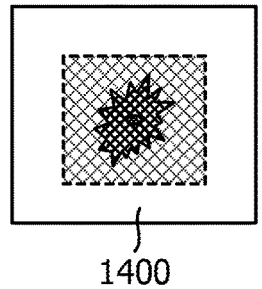
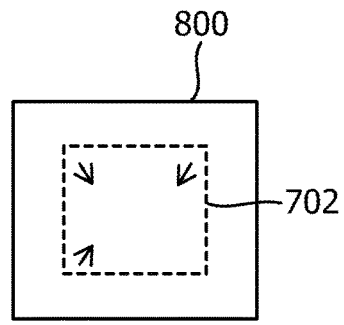
FIG. 15C-2
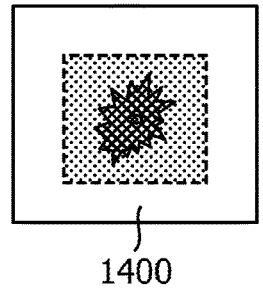

COMPUTER READABLE STORAGE MEDIUM, APPARATUS, AND METHOD FOR IMAGE PROCESSING

CROSS-REFERENCE TO RELATED APPLICATION

This application is based upon and claims the benefit of priority of the prior Japanese Patent Application No. 2015-147040, filed on Jul. 24, 2015, the entire contents of which are incorporated herein by reference.

FIELD

The embodiments disclosed herein relate to an image processing program, an image processing apparatus, and an image processing method.

BACKGROUND

In job sites of medical care, a radiologist uses computed tomography (CT) scanned images at different times to compare locations of illness or locations at which there is a suspicion of illness with each other to make a determination of illness of a patient.

CITATION LIST

[Patent Document 1] Japanese Laid-open Patent Publication No. 2013-141603

SUMMARY

According to an aspect of the invention, a non-transitory computer readable storage medium that stores a program for image processing that causes a computer to execute a process includes detecting a change in a lung based on a plurality of images of the chest scanned at different times, the change in the lung indicating that each position of each part of the lung changes toward a specified position of the lung, and outputting the change of the lung.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF DRAWINGS

FIG. 5 is a view illustrating an example of information stored in an image database (DB);

FIG. 6 is a view depicting factors of a fluctuation of a local position of a comparison destination CT image with respect to a comparison source CT image;

FIGS. 7A to 7C depict views more particularly illustrating a fluctuation of a position based on a change of a tumor;

FIG. 10 is a view depicting a functional configuration of a second registration unit;

FIG. 11 is a view illustrating process contents of a convergence region decision unit;

FIGS. 15A to 15C-2 depict views illustrating a particular example of an image processing process executed by an image processor;

DESCRIPTION OF EMBODIMENTS

Figure 1:
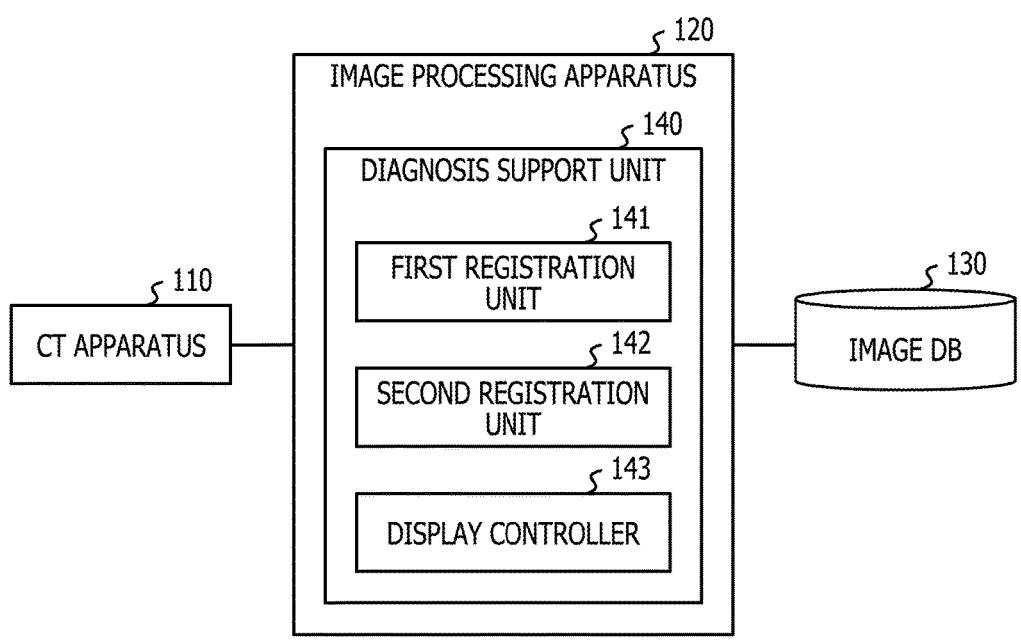
FIG. 1 is a view depicting an example of a CT imaging system.

Incidentally, where a patient has a tumor (for example, adenocarcinoma) in the lung, alveoli are collapsed by the adenocarcinoma, and surrounding such as blood vessels move so as to converge to the collapsed location. While, in a CT image, a tumor or a blood vessel is displayed white, since the lung is deformed by an influence of the breathing or the heart beating of the patient, it is difficult for a radiologist who is not experienced highly to find, on the basis of CT scanned images (or captured image) of the chest, whether or not there exists a tumor or whether or not some blood vessel is dislocated.

Therefore, it is desirable to reduce the load imposed on a radiologist when the radiologist makes a determination of a location at which some vascular convergence by an influence of alveoli collapsed due to a tumor from images of the lung deformed by an influence of the breathing or the heart beating.

In the following, embodiments are described with reference to the accompanying drawings. It is to be noted that, in the present specification and the accompanying drawings, like element having substantially like functional configurations are denoted by like reference characters and overlapping description of them is omitted herein to avoid redundancy.

First Embodiment

First, a computed tomography (CT) imaging system including an image processing apparatus according to a first embodiment is described. FIG. 1 is a view depicting an example of a CT imaging system.

A CT imaging system 100 includes a CT apparatus 110, an image processing apparatus 120, and an image database (database is hereinafter referred to as DB) 130. The CT apparatus 110 and the image processing apparatus 120 are electrically coupled to each other such that transfer of data is performed between the two apparatus. Also the image processing apparatus 120 and the image DB 130 are electrically coupled to each other such that transfer of data is performed between the two apparatus.

The CT apparatus 110 scans the inside of the body of a patient utilizing radiations and uses a computer to perform processing to generate CT images that are slice images of the patient (such a process as just described is hereinafter referred to as "to CT scan images"). The CT apparatus 110 transmits CT scanned images to the image processing apparatus 120.

The image processing apparatus 120 stores CT scanned images by the CT apparatus 110 into the coupled image DB 130. Further, the image processing apparatus 120 processes the CT scanned images by the CT apparatus 110 and displays the processed CT images to medial staff such as a radiologist. It is to be noted that the image processing apparatus 120 functions as a diagnosis support unit 140 to perform such processes as described above when a diagnosis support program, which is an example of an image processing program installed therein, is executed by a computer.

The image DB 130 receives CT scanned images by the CT apparatus 110 through the image processing apparatus 120 and stores the CT images separately for pluralities of CT scanned images (scanned image series or scanned image group) at a same time.

The diagnosis support unit 140 is a function that is utilized when a health care worker makes a diagnosis of a patient on the basis of the CT scanned images by the CT apparatus 110 and stored in the image DB 130. The diagnosis support unit 140 displays CT scanned images, for example, at different times in parallel such that the health care worker can diagnose through comparison of the CT images. It is to be noted that one of CT images displayed in parallel (for example, a CT scanned image before lapse of a given period of time) is referred to as "comparison source CT image" and another one of the CT images (for example, a CT scanned image after lapse of the given period of time) is referred to as "comparison destination CT image."

The diagnosis support unit 140 displays an image in a given region (region of interest (ROI)) including a position designated by a health care worker in the comparison source CT image in an enlarged scale on an enlarged display screen image. Further, the diagnosis support unit 140 extracts an image in a corresponding region corresponding to the given region including the designated position from within the comparison destination CT image and displays the extracted image in an enlarged scale in the enlarged display screen image. In this manner, with the diagnosis support unit 140, since an image in a given region including a designated position and an image of a corresponding region are automatically displayed in an enlarged scale, it is possible to reduce the load of the diagnosis on the health care worker and reduce the labor of the health care worker for an operation for displaying an enlarged image.

It is to be noted that, in order to execute such processes as described above, the diagnosis support unit 140 includes a first registration unit 141, a second registration unit 142, and a display controller 143.

The first registration unit 141 is implemented, for example, by a first registration program executed by a computer. The first registration unit 141 corrects, when CT scanned images at different times are displayed in parallel, positional displacement between the CT images by using affine transformation to perform global positioning between the CT images.

The second registration unit 142 is implemented, for example, by a second registration program executed by the computer. The second registration unit 142 performs, when an image in a given region including a position designated by the health care worker is displayed in an enlarged scale, a conversion process for the comparison destination CT image to perform local positioning and extracts an image in a corresponding region from the comparison destination CT image.

Consequently, the second registration unit 142 can notify the display controller 143 of the image in the corresponding region. It is to be noted that, although the conversion process includes various processes, the conversion process in the present embodiment is parallel movement, and an image in a corresponding region extracted from the comparison destination CT image by performing a conversion process is referred to as "image for which local positioning has been performed."

Further, if an instruction for image processing is received from the health care worker, then the second registration unit 142 performs an image processing process for promoting an appropriate diagnosis by a health care worker for a tumor regarding the image in the corresponding region.

Consequently, the second registration unit 142 can notify the display controller 143 of the image in the corresponding region for which the image processing process has been performed.

The display controller 143 is implemented, for example, by a display program executed by the computer. The display controller 143 displays a comparison source CT image selected by the health care worker and displays a given region including a position designated by the health care worker in an enlarged scale on the enlarged display screen image. Further, the display controller 143 displays the image, which has been noticed from the second registration unit 142 and for which local positioning has been performed (in the case where an image processing process has been performed, the image after the image processing process is performed), in an enlarged scale on the enlarged display screen image.

Figure 2:
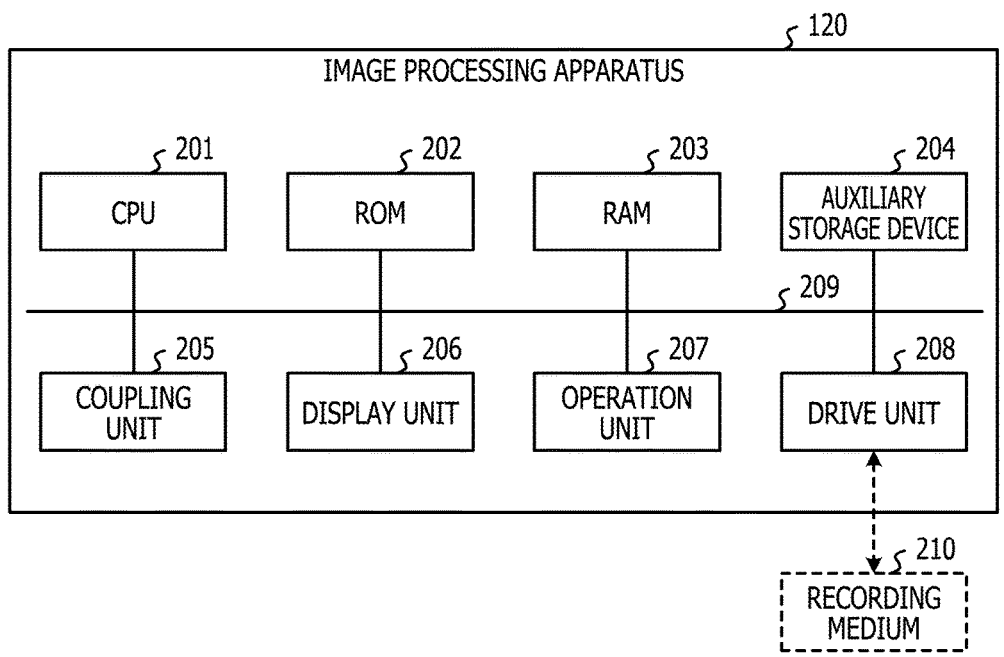
FIG. 2 is a view depicting a hardware configuration of an image processing apparatus.

Now, a hardware configuration of the image processing apparatus 120 is described. FIG. 2 is a view depicting a hardware configuration of an image processing apparatus. The image processing apparatus 120 includes a central processing unit (CPU) 201, a read only memory (ROM) 202, and a random access memory (RAM) 203, as depicted in FIG. 2. The image processing apparatus 120 further includes an auxiliary storage unit 204, a coupling unit 205, a display unit 206, an operation unit 207, and a drive unit 208. It is to be noted that the components of the image processing apparatus 120 are coupled to each other by a bus 209.

The CPU 201 is a computer that executes various programs stored in the auxiliary storage unit 204 (for example, a first registration program, a second registration program, a display program and so forth).

The ROM 202 is a nonvolatile memory. The ROM 202 functions as a main storage unit for storing various programs, data and so froth used for the CPU 201 to execute the various programs stored in the auxiliary storage unit 204. For example, the ROM 202 stores boot programs such as a basic input/output system (BIOS) or an extensible firmware interface (EFI) and so forth therein.

The RAM 203 is a volatile memory and includes a dynamic random access memory (DRAM), a static random access memory (SRAM) and so forth. The RAM 203 is a main storage unit that provides a working area in which various programs stored in the auxiliary storage unit 204 are developed when the various programs are to be executed by the CPU 201.

The auxiliary storage unit 204 is a computer-readable storage apparatus into which various programs installed in the image processing apparatus 120 and data and so forth generated by execution of the various programs are recorded.

The coupling unit 205 is coupled with the CT apparatus 110 and the image DB 130 and transfers data to and from the CT apparatus 110 and the image DB 130. The display unit 206 displays a CT scanned image by the CT apparatus 110 and stored in the image DB 130 through a parallel display screen image. The operation unit 207 accepts various operations performed from the image processing apparatus 120 by a health care worker.

The drive unit 208 is a device for setting a recording medium 210 set therein. The recording medium 210 here includes media in which information is optically, electrically, or magnetically recorded like a compact disc (CD)-ROM, a flexible disk, or a magneto-optical disk. Further, the recording medium 210 includes semiconductor memories for electrically recording information like a ROM, a flash memory and so forth.

It is to be noted that, in the present embodiment, the various programs stored in the auxiliary storage unit 204 are installed by loading, for example, a distributed recording medium 210 into the drive unit 208 and reading out the various programs recorded in the recording medium 210 by the drive unit 208 or by downloading various programs from the network through the coupling unit 205.

Now, a relationship of processing contents of the diagnosis support unit 140 of the image processing apparatus 120, operation contents of a health care worker, and a parallel display screen image displayed on the display unit 206 of the image processing apparatus 120 when a process is executed by the diagnosis support unit 140 is described.

Figure 3:
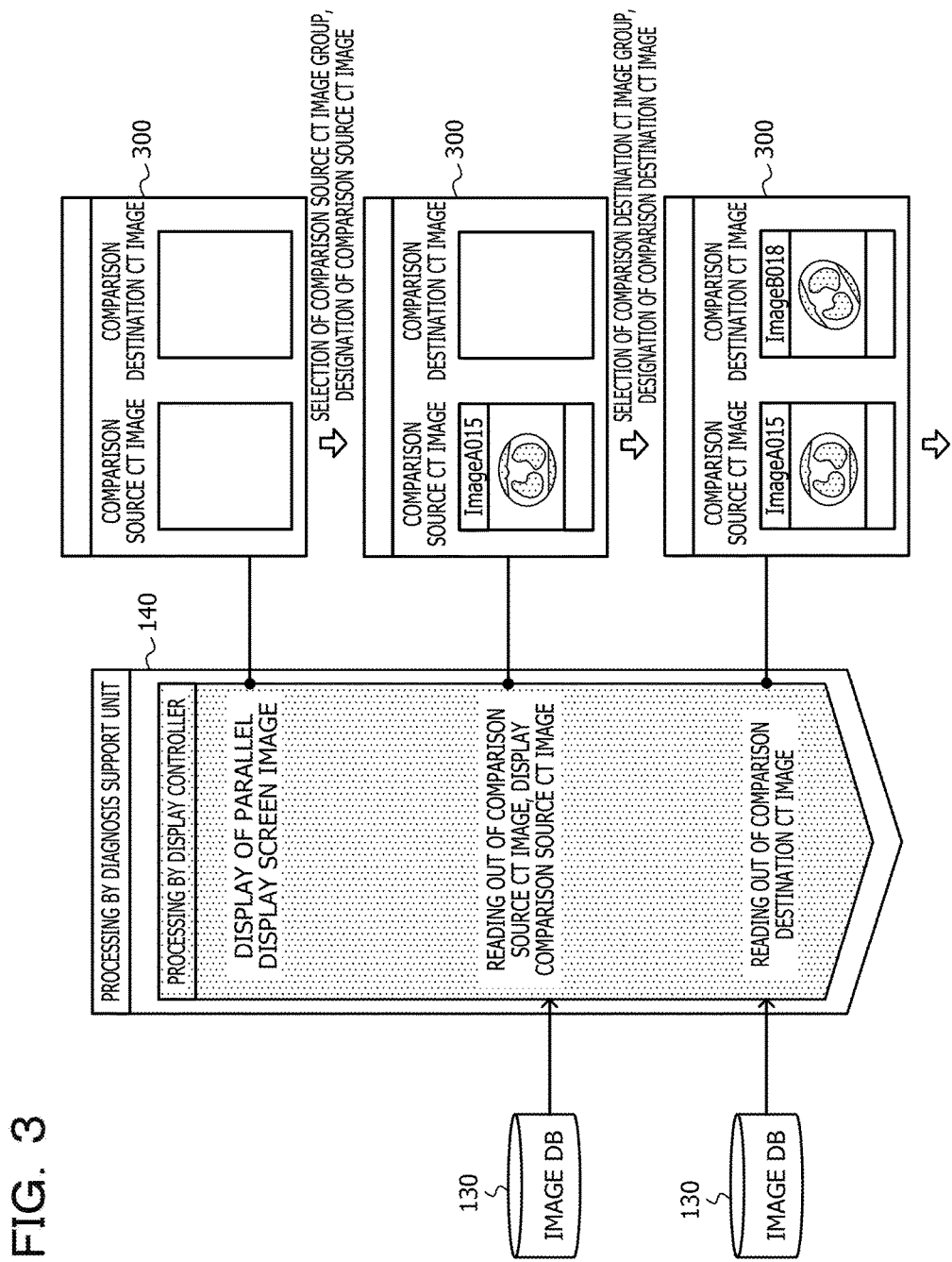
FIG. 3 is a view illustrating a relationship among process contents of a diagnosis support unit of an image processing apparatus, operation contents of a health care worker, and display contents of a parallel display screen image.
Figure 4:
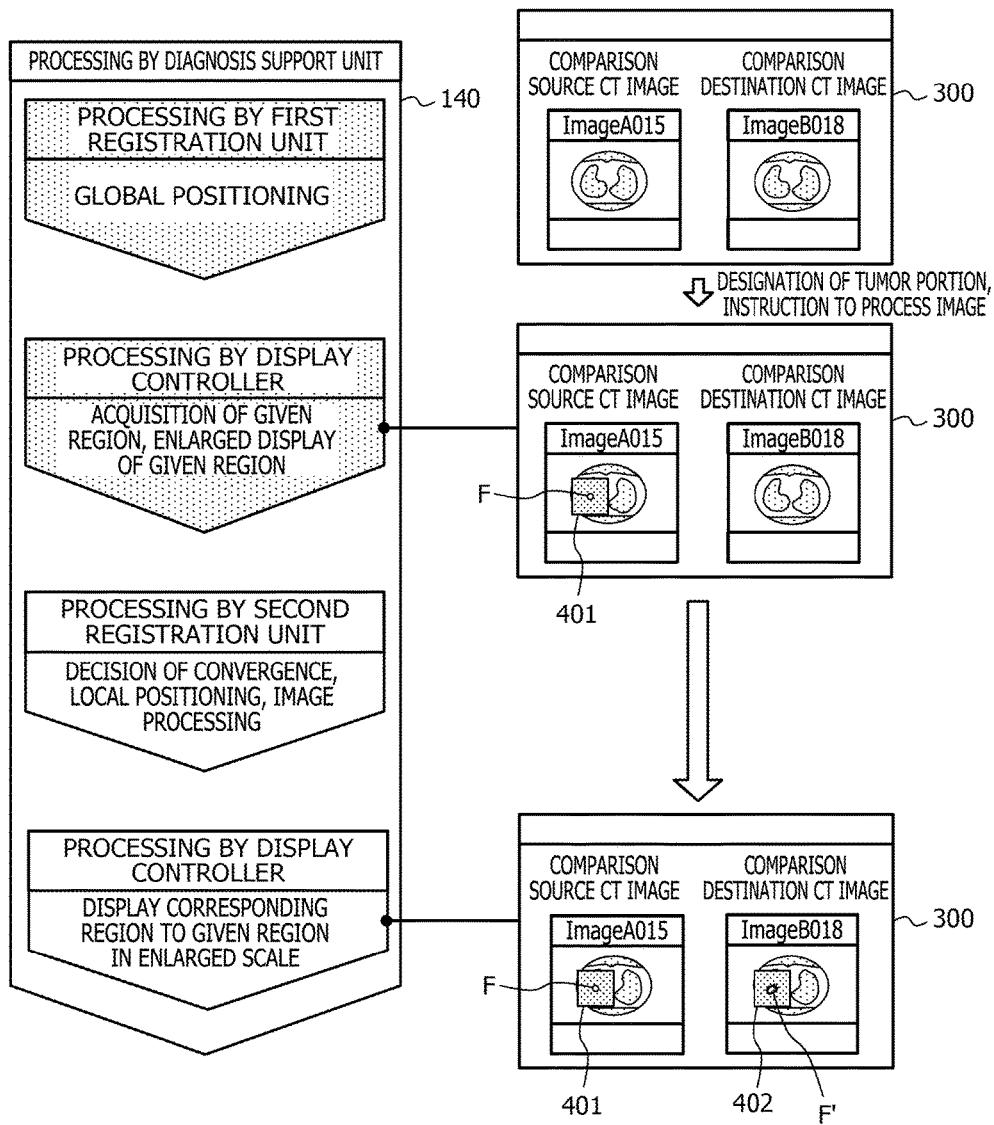
FIG. 4 is a view illustrating a relationship among process contents of a diagnosis support unit of an image processing apparatus, operation contents of a health care worker, and display contents of a parallel display screen image.

FIGS. 3 and 4 are views illustrating relationships among processing contents of a diagnosis support unit of an image processing apparatus, operation contents of a health care worker, and display contents of a parallel display screen image.

In the image processing apparatus 120, if the diagnosis support unit 140 is activated, then processing by the display controller 143 is started, and a parallel display screen image 300 for displaying CT scanned images at different times in parallel is displayed on the display unit 206 as depicted in FIG. 3. In a state in which the parallel display screen image 300 is displayed, a health care worker would select a scanned image series of a given region (here, of the chest) of a given patient scanned at given time as a comparison source CT image series. Consequently, the display controller 143 reads out the selected comparison source CT image series from the image DB 130. Further, if a given comparison source CT image (here, file name="ImageA015") is designated from within the selected comparison source CT image series by the health care worker, then the display controller 143 displays the designated comparison source CT image in the parallel display screen image 300.

In order to compare with the designated comparison source CT image, the health care worker would select a scanned image series of a same region of the same patient scanned at a different time as a comparison destination CT image series. For example, the health care worker would input a patient identification (ID), series date and time, a body part examined (here, the chest) and so forth for selection. Consequently, the display controller 143 reads out the scanned image series specified by the inputted patient name, series date and time, body part examined and so forth as a comparison destination CT image series from the image DB 130. Further, the display controller 143 reads out a comparison destination CT image (here, file name="ImageB018") corresponding to the comparison source CT image displayed in the parallel display screen image 300 from within the read out comparison destination CT image series and displays the comparison destination CT image in the parallel display screen image 300.

At this time, in the diagnosis support unit 140, the first registration unit 141 functions to perform correction using affine transformation such as rotation or parallel translation for the read out CT image to perform global positioning. Since global positioning is performed for the entire CT image, global positional displacement between the comparison source CT image and the comparison destination CT image is reduced.

After the global positioning is completed, the health care worker would designate a position of a tumor F in the displayed comparison source CT image as depicted in FIG. 4. Consequently, the display controller 143 displays an image of a given region (region of interest (ROI)) 401 including the position of the designated tumor F in an enlarged scale in the enlarged displace screen image in the comparison source CT image. Further, at this time, the health care worker would additionally designate whether or not image processing is to be performed.

After an image of the given region (ROI) 401 is displayed in an enlarged scale, the second registration unit 142 performs local positioning for a partial region of the comparison destination CT image. Consequently, the second registration unit 142 extracts an image of a corresponding region 402 including a position of a tumor F' corresponding to the tumor F (image for which local positioning has been performed). It is to be noted that the second registration unit 142 performs convergence decision (details are hereinafter described) before the local positioning is performed.

Further, if an instruction for image processing is issued from the health care worker, then the second registration unit 142 performs an image processing process (details are hereinafter described) for the image in the corresponding region 402 obtained by performing the local positioning.

Further, the second registration unit 142 notifies the display controller 143 of the image in the corresponding region 402 obtained by performing the local positioning (in the case where an image processing process has been executed, the image after the image processing process).

The display controller 143 displays the image in the corresponding region 402 notified from the second registration unit 142 (in the case where an image processing process has been executed, the image after the image processing process) in an enlarged scale on the enlarged display screen image in the comparison destination CT image. Consequently, the image for which the local positioning has been performed and besides the image processing has been performed can be displayed.

In this manner, with the image processing apparatus 120, when the position of the tumor F is designated on the comparison source CT image by the health care worker, an image in the given region 401 can be displayed in an enlarged scale. Further, it is possible to extract an image in the corresponding region 402 from the comparison destination CT image by performing local positioning on the basis of an image in the given region 401 and perform image processing for promoting appropriate diagnosis by a health care worker for a tumor and then display the image in an enlarged scale on the enlarged display screen image.

Consequently, it becomes possible for the health care worker to easily grasp a corresponding region between CT images included in scanned image series at different times and to perform appropriate diagnosis for the tumor.

Now, the image DB 130 is described. FIG. 5 is a view illustrating an example of information stored in an image DB. As illustrated in FIG. 5, information stored in the image DB 130 is managed in a classified state for each patient, and FIG. 5 illustrates an example of information relating to a patient of a patient ID="xxx."

As depicted in FIG. 5, items of information of a patient include "series date and time," "body part examined," "series name," and "image list." In the "series date and time," information regarding the date and time at which the CT image was scanned is placed. In the "body part examined," information regarding the body part of the CT scanning target is placed. In the "series name," a series name for specifying a series configured from a plurality of CT scanned images is placed. In the "image list," a plurality of CT scanned images (file names) are placed.

The example of FIG. 5 indicates that a series of the series name="series A" including CT images ImageA001 to ImageA030 obtained by CT scanning for the body part examined="chest" at the series date and time="Feb. 5, 2014" is placed in the image DB 130. The example of FIG. 5 further indicates that a series of the series name="series B" including CT images ImageB001 to ImageB030 obtained by CT scanning for the body part examined="chest" at the series date and time="Aug. 3, 2015" is placed in the image DB 130.

It is to be noted that a broken line in FIG. 5 indicates that the CT image of "ImageA015" is selected as a comparison source CT image by a health care worker. Further, it is indicated that the CT image of "ImageB018" is selected as a comparison destination CT image by a health care worker.

Now, individual portions of the diagnosis support unit 140 are described. It is to be noted that, in the following, description is given principally of the second registration unit 142.

As described hereinabove, at the point of time at which the global positioning is completed, the comparison source CT image and the comparison destination CT image are corrected against a general positional fluctuation while a local positional fluctuation remains. Therefore, when an image in the corresponding region 402 corresponding to the given region 401 including the position of the tumor F designated by the health care worker is to be displayed in an enlarged scale, the second registration unit 142 first determines a local positional fluctuation of the comparison destination CT image with respect to the comparison source CT image. Then, the second registration unit 142 performs a conversion process by parallel translation in the comparison destination CT image in response to the determined fluctuation to perform local positioning. Consequently, the second registration unit 142 can extract the image of the corresponding region 402.

Here, where the body part examined="chest," a fluctuation of a local position is caused by two available principal factors (one of which is based on the breathing or the heart beating and the other of which is based on a change (time-dependent variation) of a tumor). FIG. 6 is a view illustrating factors of a local positional fluctuation of a comparison destination CT image with respect to a comparison source CT image.

If a local positional fluctuation occurs as depicted in FIG. 6, then in a region of a comparison destination CT image having same coordinates as those of a given region 401 of a comparison source CT image, for example, an image 610 is displayed.

If an image 600 in the given region 401 of the comparison source CT image and the image 610 in a region of the comparison destination CT image having coordinates same as those of the given region 401 are compared with each other in FIG. 6, then it can be recognized that the position of a blood vessel and the position of a tumor (namely, each position of each part of the lung) are displaced by a great amount by a local positional fluctuation. In FIG. 6, thick lines denote blood vessels 601 to 603 and 611 to 613, and shadowed regions indicate tumors F and F'.

It is to be noted that the positional fluctuation based on the breathing and the heart beating is a fluctuation of the position caused by a movement of the diaphragm, for example, upon breathing. Since the position of the diaphragm is fluctuated depending upon whether a patient exhales or inhales, the position of portions of the lung is fluctuated by the fluctuation of the position of the diaphragm. In particular, the comparison source CT image and the comparison destination CT image can include there between a fluctuation of a local position based on the breathing and the heart beating except when the breathing states of the patient upon image scan coincide fully with each other.

It is to be noted that, although the positional fluctuation based on the breathing and the heart beating is non-rigid deformation, for example, with respect to the entire body, since the given region 401 is part of the inside of the lung, the entire given region 401 translates in parallel in a given direction. Accordingly, the positional fluctuation can be regarded as rigid-body motion.

On the other hand, the positional fluctuation based on a change of a tumor is a fluctuation of the position of the tumor arising from that a malignant tumor such as adenocarcinoma grows while destroying the alveoli and the volume of the alveoli decreases by an amount of air having been held by the alveoli (in other words, involved in convergence occurring in the tumor).

The second registration unit 142 subtracts a fluctuation amount of the position based on a change of the tumor (time-dependent change) from between the positional fluctuations based on the two factors described above to extract a fluctuation amount of the position based on the breathing and the heart beating. Then, the second registration unit 142 performs local positioning based on the fluctuation amount of the position based on the breathing and the heart beating.

Here, a change (time-dependent variation) of a tumor is described in more detail with reference to FIG. 7. FIG. 7 depict views illustrating a positional fluctuation based on a change of a tumor in more detail.

FIG. 7A illustrates a manner of surrounding tissues immediately after a malignant tumor such as adenocarcinoma is generated at a position indicated at a tumor central point O. As illustrated in FIG. 7A, in a state immediately after the malignant tumor is generated, both of the distance from the tumor central point O to a point $D_1$ of bronchus 711 and the distance from the tumor central point O to a point $C_1$ of a blood vessel 712 are r1.

FIG. 7B illustrates a manner in which, since the malignant tumor grows while destroying the alveolus around the tumor, surrounding tissues including the bronchus 711 and the blood vessel 712 move toward the tumor central point O. As depicted in FIG. 7B, as a result of the movement of the surrounding tissues toward the tumor central point O, both of the distance from the tumor central point O to a point $D_2$ of the bronchus 711 and the distance from the tumor central point O to a point $C_2$ of the blood vessel 712 become r2 (<r1).

FIG. 7C illustrates a manner in which, since the malignant tumor further glows while destroying the alveolus around the tumor, the surrounding tissues including the bronchus 711 and the blood vessel 712 further move toward the tumor central point O. As depicted in FIG. 7C, as a result of the movement of the surrounding tissues toward the tumor central point O, both of the distance from the tumor central point O to a point $D_3$ of the bronchus 711 and the distance from the tumor central point O to a point $C_3$ of the blood vessel 712 become r3 (<r2).

In this manner, a fluctuation of a position based on a change of a tumor (involved in convergence caused by the tumor) has a characteristic that surrounding tissues move toward the tumor central point O and can be regarded as non-rigid deformation.

It is to be noted that, as depicted in FIG. 7, tissues around the tumor can be roughly classified into tissues of a tumor region 703, tissues in a convergence region 702, and tissues in a normal region 701. In the tumor region 703, since the tissues are destroyed by the newly appearing malignant tumor, part of the tissues existing in FIG. 7A disappears and does not exist in FIG. 7C. Meanwhile, in the convergence region 702, although tissues existing in FIG. 7A exist also in FIG. 7C, it can be regarded that the position of the corresponding tissues is fluctuated in a direction toward the center ($B_1 \rightarrow B_2 \rightarrow B_3$). Further, in the normal region 701, tissues existing in FIG. 7A still exist in FIG. 7C, and the position ($A_1 \rightarrow A_2 \rightarrow A_3$) of the corresponding tissues is little fluctuated.

As apparently recognized from the description given above with reference to FIGS. 6 and 7, the factors of a local positional fluctuation between a comparison source CT image and a comparison destination CT image include a "factor based on the breathing and the heart beating" which can be regarded as rigid-body motion and a "factor based on a change of a tumor" which is a non-rigid deformation. Further, where the "factor based on a change of a tumor," there is a characteristic that surrounding tissues move toward the tumor central point O, and tissues around the tumor can be roughly classified into tissues in the normal region 701, the convergence region 702, and the tumor region 703 in accordance with the degree.

Now, problems when the second registration unit 142 performs local positioning for a region in which such a rigid-body motion and non-rigid deformation as depicted in FIG. 6 exist in a mixed state in a comparison destination CT image are described with reference to FIGS. 8 and 9.

As described hereinabove, when local positioning is to be performed in a comparison destination CT image, the second registration unit 142 performs a conversion process by parallel translation. In other words, the second registration unit 142 performs not a conversion process assuming a non-rigid body but a conversion process assuming a rigid body.

Here, when to perform a conversion process by parallel translation, the second registration unit 142 performs calculation of a representative vector indicative of to which position of the comparison destination CT image the given region 401 moves (positional relationship between the given region 401 and the corresponding region 402).

FIG. 8 depict views illustrating a calculation process of a representative vector and a calculation process of a corresponding region. In particular, FIG. 8A illustrates a corresponding vector (dark arrow mark) that is the difference between the position of a feature point included in the given region 401 of the comparison source CT image and the position of a feature point in the comparison destination CT image corresponding to the feature point. It is to be noted that a region 800 is a region in which a feature point in the comparison destination CT image corresponding to the feature point included in the given region 401 of the comparison source CT image is included, and is a region used for calculation of a representative vector. In the following, the region in the comparison destination CT image is referred to as representative vector calculation target region 800.

Here, it is assumed that the second registration unit 142 calculates a representative vector 810 using all corresponding vectors included in the representative vector calculation target region 800. In this case, an image for which local positioning has been performed can be extracted by executing a process illustrated in FIG. 8B.

Figure 8A:
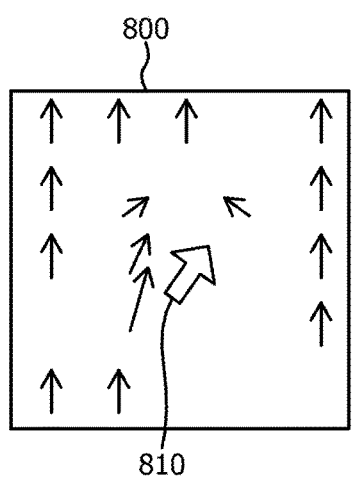
FIGS. 8A to 8D depict views illustrating a calculation process of a representative vector and a calculation process of a corresponding region.
Figure 8B:
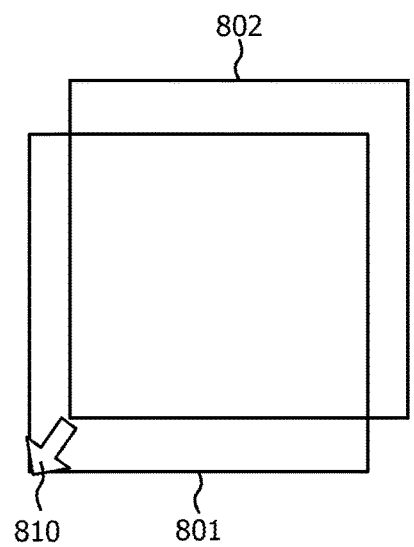

FIG. 8B illustrates a manner in which an image for which local positioning has been formed from a comparison destination CT image is extracted by performing a conversion process by parallel translation using the representative vector 810. As depicted in FIG. 8B, the second registration unit 142 determines a region 802 by parallelly translating a region 801 in the comparison destination CT image having coordinates same as those of the given region 401 of the comparison source CT image on the basis of the representative vector 810. Then, the second registration unit 142 extracts an image of the region 802 from the comparison destination CT image to extract an image for which local positioning has been performed.

However, the image extracted in this manner is nothing but an image obtained by determining a representative vector assuming that only a rigid-body motion occurs in a region in which a rigid body motion and non-rigid deformation exist in a mixed manner and then parallelly translating the image so as to cancel the assumed rigid-body motion. In short, the parallel translation is performed so as to cancel also the influence of the non-rigid deformation amount.

Figure 8C:
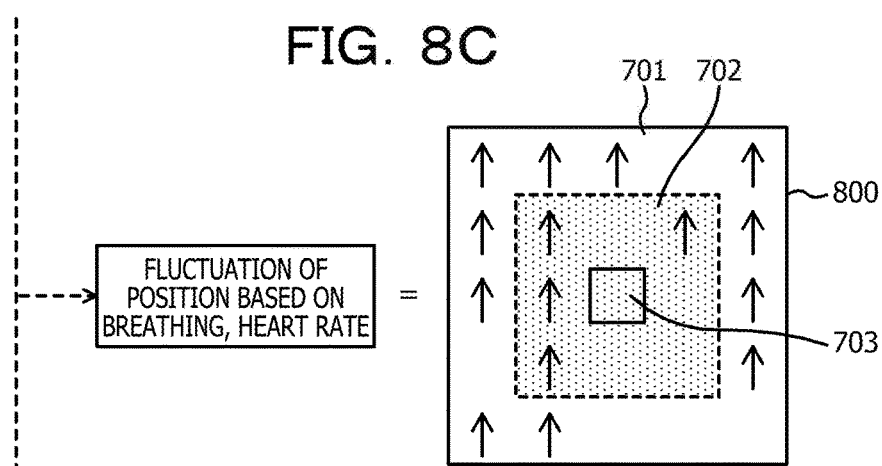
Figure 8D:
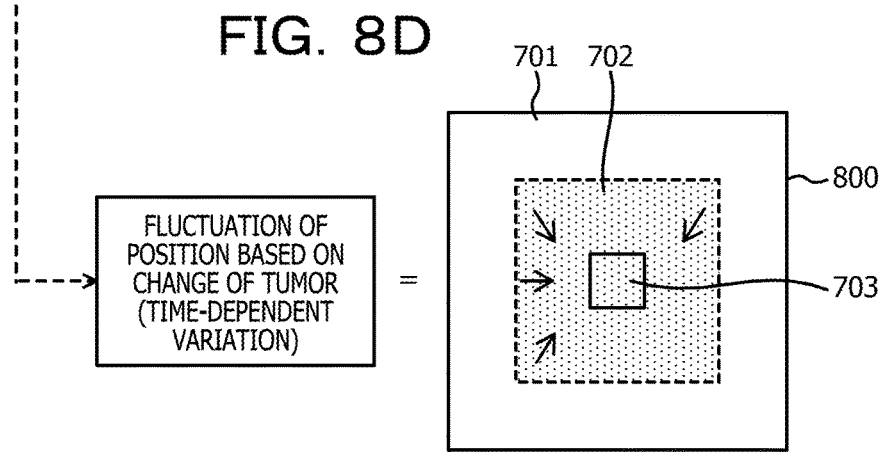

More detailed description is given with reference to FIGS. 8C and 8D. FIG. 8C illustrates corresponding vectors of fluctuation amounts (rigid-body motion amounts) of positions based on the breathing and the heart beating from among corresponding vectors each of which links the position of a feature point included in the given region 401 of the comparison source CT image and the position of a feature point in the comparison destination CT image corresponding to the feature point. As depicted in FIG. 8C, the corresponding vectors of the rigid body motion amounts are directed in the same direction and have an equal length. It is to be noted that the corresponding vectors of the rigid motion amounts exist in the normal region 701 and the convergence region 702. However, since a feature point of the comparison destination CT image corresponding to a feature point of the comparison source CT image does not exist in the tumor region 703, no corresponding vector exists in the tumor region 703.

Meanwhile, FIG. 8D illustrates corresponding vectors of fluctuation amounts (non-rigid deformation amounts) of positions based on a change of the tumor from among corresponding vectors that link the positions of the feature points included in the given region 401 of the comparison source CT image and the positions of feature points in the comparison destination CT image corresponding to the feature points. As depicted in FIG. 8D, a corresponding vector of a non-rigid deformation amount exists only in the convergence region 702 (in this regard, except the tumor region 703) and can be regarded as being directed toward the center.

In this manner, the corresponding vectors corresponding to the rigid body motions and the corresponding vectors corresponding to the non-rigid deformations are different in length and direction of a vector from each other and are different also in existing position.

On the other hand, the corresponding vectors illustrated in FIG. 8A are sums of the corresponding vectors depicted in FIG. 8C and the corresponding vectors depicted in FIG. 8D.

In particular, the corresponding vectors existing at a position corresponding to the convergence region 702 from among the corresponding vectors depicted in FIG. 8A include the corresponding vectors corresponding to rigid-body motions and the corresponding vectors corresponding to the non-rigid deformations in a mixed state. Therefore, if the representative vector 810 is calculated from corresponding vectors including the corresponding vectors existing at the position corresponding to the convergence region 702, then the representative vector 810 includes an influence of non-rigid deformation. Even if such a representative vector 810 as just described is used to perform local positioning, positioning of high accuracy is not expectable.

Description is given using a particular image. FIG. 9 is a view depicting an image for which local positioning has been performed using a representative vector including an influence of non-rigid deformation. It is to be noted that, in the example of FIG. 9, an image 900 for which local positioning has been performed (image of the region 802 of the comparison destination CT image) and the image 600 of the given region 401 of the comparison source CT image are depicted in an overlapping relationship with each other.

Figure 9:
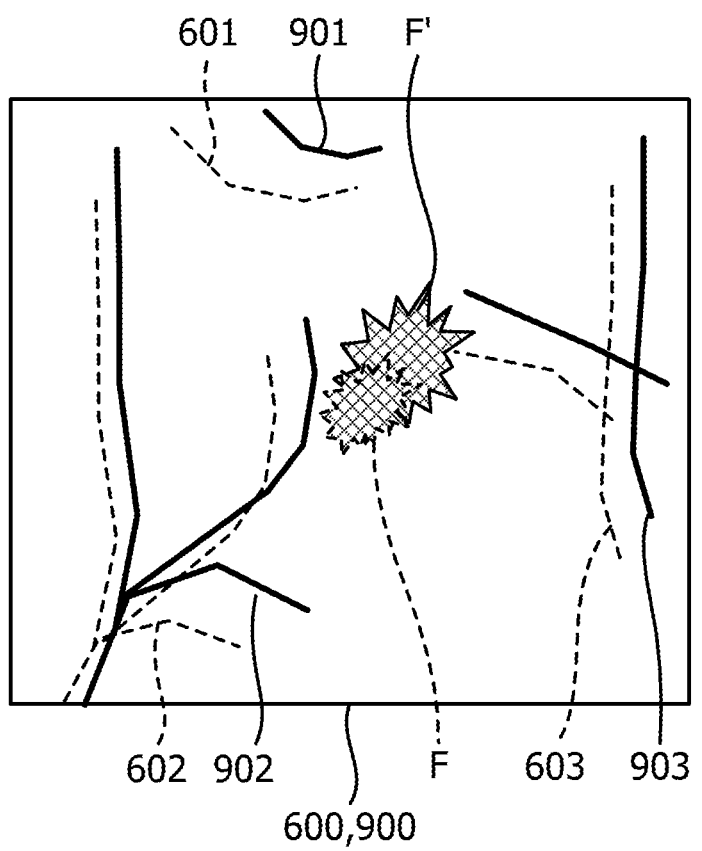
FIG. 9 is a view depicting an image for which local positioning has been performed using a representative vector including an influence of non-rigid deformation.

As depicted in FIG. 9, the positions of blood vessels 901 to 903 and a tumor F' included in the image 900 are displaced from the positions of the blood vessels 601 to 603 and the tumor F included in the image 600 although local positioning has been performed.

Taking the problem in calculation of a representative vector in such a region in which rigid-body motions and non-rigid deformations exist in a mixed manner as described above into consideration, the second registration unit 142 in the present embodiment determines a representative vector removing an influence of non-rigid deformation and performs local positioning. Further, the second registration unit 142 in the present embodiment performs an image processing process for an image of the corresponding region 402 obtained by performing the local positioning to visualize and display an influence of the non-rigid deformation (namely, a fluctuation amount of a position based on a change of the tumor (time-dependent variation)).

In the following, a functional configuration of the second registration unit 142 in the present embodiment is described with reference to FIG. 10, and functions of components of the second registration unit 142 are described with reference to FIGS. 11 to 15. Further, details of processes executed by the second registration unit 142 are described with reference to flowcharts of FIGS. 16 to 19.

FIG. 10 is a view depicting a functional configuration of a second registration unit. As depicted in FIG. 10, the second registration unit 142 includes a region identification unit 1001, a corresponding vector calculation unit 1002, a convergence region decision unit 1003, a representative vector calculation unit 1004, a positioning unit 1005, and an image processor 1006.

The region identification unit 1001 identifies a given region 401 including a position designated by a health care worker. For example, the region identification unit 1001 acquires coordinates on a comparison source CT image which specify the position of the given region 401.

The corresponding vector calculation unit 1002 extracts feature points from the given region 401 of the comparison source CT image identified by the region identification unit 1001. Further, the corresponding vector calculation unit 1002 searches for feature points in a comparison destination CT image corresponding to the extracted feature points. Further, the corresponding vector calculation unit 1002 calculates corresponding vectors on the basis of a difference of the positions of the feature points extracted from the comparison source CT image and the positions of the feature points in the comparison destination CT image corresponding to the feature points.

The convergence region decision unit 1003 decides whether or not a convergence region 702 is included in the representative vector calculation target region 800 on the basis of the corresponding vectors calculated by the corresponding vector calculation unit 1002. Further, if it is decided that the convergence region 702 is included, then the convergence region decision unit 1003 calculates a boundary position between the normal region 701 and the convergence region 702. Further, the convergence region decision unit 1003 notifies the representative vector calculation unit 1004 of a result of the decision of whether or not a convergence region 702 is included and a result of the calculation of the boundary position between the normal region 701 and the convergence region 702.

The representative vector calculation unit 1004 calculates a representative vector in the representative vector calculation target region 800 on the basis of the corresponding vectors calculated by the corresponding vector calculation unit 1002. If it is decided that a convergence region 702 is not included in the representative vector calculation target region 800, then the representative vector calculation unit 1004 calculates a representative vector using all corresponding vectors in the representative vector calculation target region 800 (in this regard, except the tumor region). On the other hand, if it is decided that a convergence region 702 is included in the representative vector calculation target region 800, then the representative vector calculation unit 1004 calculates a representative vector using the corresponding vectors in the representative vector calculation target region 800 except the corresponding vectors included in the convergence region (and the tumor region).

It is to be noted that, in the present embodiment, the representative vector calculation unit 1004 performs an averaging process when it is to calculate a representative vector using the corresponding vectors.

The positioning unit 1005 extracts an image of a corresponding region 402 corresponding to the given region 401 from the comparison destination CT image on the basis of the representative vector calculated by the representative vector calculation unit 1004. For example, the positioning unit 1005 moves the coordinates that specify the position of the given region 401 using the representative vector on the comparison destination CT image to calculate the coordinates after the movement. Further, the positioning unit 1005 acquires an image for which local positioning has been performed by extracting the image of the region (corresponding region 402) specified by the calculated coordinates after the movement from the comparison destination CT image.

The image processor 1006 performs image processing of the image of the corresponding region 402 obtained by performing the local positioning for visualizing the fluctuation amount of the position based on a change of the tumor (time-dependent variation). If an instruction for image processing from a health care worker is issued, then the image processor 1006 performs image processing for the image of the corresponding region 402.

For example, the image processor 1006 visualizes a change of a tissue based on a change of the tumor by calculating a difference between pixel values between the image of the given region 401 and the image of the corresponding region 402. Further, the image processor 1006 visualizes a moving direction and a movement amount of the tissue based on the change of the tumor by calculating a vector indicative of a fluctuation of the position based on the change of the tumor between the image of the given region 401 and the image of the corresponding region 402. Further, the image processor 1006 visualizes a tendency of the change of the tissue based on the change of the tumor on the basis of a distribution of the calculated vectors in the corresponding region 402.

It is to be noted that the image processor 1006 notifies the display controller 143 of the image of the corresponding region 402 for which the image processing has been performed. Consequently, the display controller 143 can cause an image obtained by performing the image processing for the image of the corresponding region obtained by the local positioning to be displayed in an enlarged scale on the enlarged display screen image.

Now, a particular example of the functions of the convergence region decision unit 1003, the representative vector calculation unit 1004, the positioning unit 1005, and the image processor 1006 from among the components included in the second registration unit 142 depicted in FIG. 10 is described.

First, a particular example of functions of the convergence region decision unit 1003 is described. FIG. 11 is a view illustrating processing contents of a convergence region decision unit.

FIG. 11 illustrates a manner in which the representative vector calculation target region 800 is partitioned by delimiting lines of a given step size into rectangular frame shapes from the center to side edges of the representative vector calculation target region 800 and it is decided on the basis of corresponding vectors of the partitions whether or not a convergence region 702 is included in the representative vector calculation target region 800.

It is to be noted that the distance from the center to a side edge of the representative vector calculation target region 800 is represented by R, and the step size is represented by $\Delta R$. Further, while a case in which the representative vector calculation target region 800 is partitioned into rectangular frame shapes is described, the representative vector calculation target region 800 may be partitioned into ring shapes instead of rectangular frame shapes.

The convergence region decision unit 1003 extracts corresponding vectors included in a partition group 1101 within the range of R to (R−$\Delta R$) (shadowed region in the representative vector calculation target region 800 depicted on the left side in FIG. 11). Further, the convergence region decision unit 1003 extracts corresponding vectors included in a partition group 1102 within the range of (R−$\Delta R$) to (R−$\Delta R$× 2) (shadowed region in the representative vector calculation target region 800 depicted at the center in FIG. 11).

Further, the convergence region decision unit 1003 calculates a difference between each corresponding vectors adjacent each other between the corresponding vectors of the partition group 1101 and the corresponding vectors of the partition group 1102 from among the extracted corresponding vectors to determine difference vectors. It can be considered that the difference vector here indicates a difference in change of the position of a feature point between the comparison source CT image and the comparison destination CT image. The vectors in the representative vector calculation target region 800 depicted on the right side in FIG. 11 indicate an example of difference vectors calculated on the basis of the corresponding vectors of the partition group 1101 and the corresponding vectors of the partition group 1102.

If each difference vector determined in this manner is greater than a given threshold value, then the convergence region decision unit 1003 decides a direction of the difference vector. Further, if the direction of the difference vector can be regarded as being directed toward the center of the representative vector calculation target region 800 (which represents a collapsing change), then the convergence region decision unit 1003 decides that a convergence region is included (namely, the convergence region decision unit 1003 detects a convergence region). Further, the convergence region decision unit 1003 decides a boundary position between two partition groups in which the corresponding vectors for calculating the difference vectors used for the decision that a convergence region is included exist as the boundary position between the normal region and the convergence region.

It is to be noted that, as apparent from the description given above with reference to FIG. 11, the convergence region decision unit 1003 first determines a difference vector using corresponding vectors extracted from the partition group 1101 positioned at the outermost side of the representative vector calculation target region 800. This is because the corresponding vectors can be estimated as corresponding vectors involved in a fluctuation of the position based on the breathing and the heart beating, which are not influenced by a fluctuation of the position based on a change of the tumor.

Further, the convergence region decision unit 1003 calculates a difference between adjacent corresponding vectors. This is because there is no great difference in fluctuation of the position based on the breathing and the heart beating between adjacent corresponding vectors and, by calculating the difference, an influence of the fluctuation of the position based on the breathing and the heart beating can be cancelled. In other words, it can be considered that a difference vector determined by calculating the difference between adjacent corresponding vectors (it is to be noted that the difference vector has a magnitude equal to or greater than a given threshold value) represents a corresponding vector corresponding to a fluctuation amount of the position based on a change of the tumor.

It is to be noted that the reason why the convergence region decision unit 1003 decides a direction of a difference vector is that, because a corresponding vector in a convergence region has a property that it is directed toward the tumor central point O, this is effective to identify (or detect) that the corresponding vector is a fluctuation of the position based on the change of the tumor.

Now, a particular example of the function of the representative vector calculation unit 1004 is described. FIG. 12 depict views illustrating a calculation method of a representative vector when it is decided that a convergence region exists.

Figure 12A:
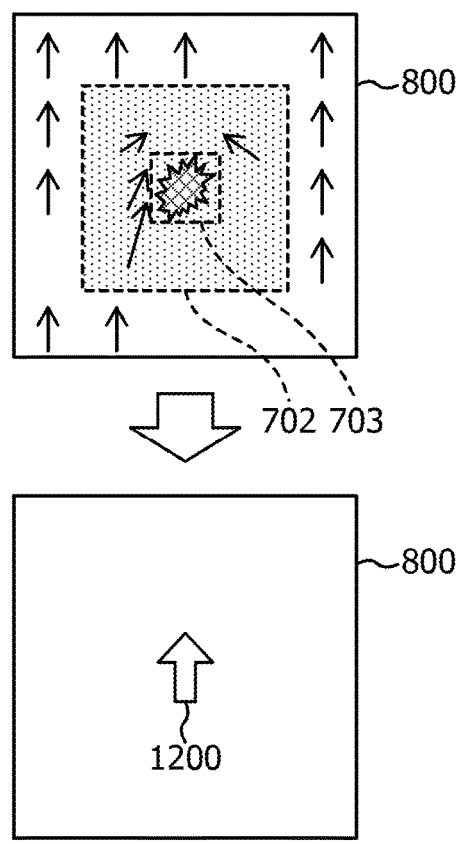
FIGS. 12A and 12B depict views illustrating a calculation method of a representative vector when it is decided that there exists a convergence region.

If the representative vector calculation target region 800 includes a convergence region 702, then the representative vector calculation unit 1004 determines a representative vector from among corresponding vectors calculated by the representative vector calculation target region 800 except the corresponding vectors existing in the convergence region 702. In the example of FIG. 12A, 15 corresponding vectors (indicated by dark arrow marks) are calculated by the representative vector calculation target region 800, and the representative vector calculation unit 1004 calculates a representative vector using 11 corresponding vectors excluding the four corresponding vectors existing in the convergence region 702 from among the 15 corresponding vectors.

A representative vector 1200 indicates a representative vector calculated using the 11 corresponding vectors. In this manner, by excluding the four corresponding vectors existing in the convergence region 702, a representative vector can be determined excluding the influence of non-rigid deformation (namely, a fluctuation amount of the position based on the change of the tumor (time-dependent change)).

Figure 12B:
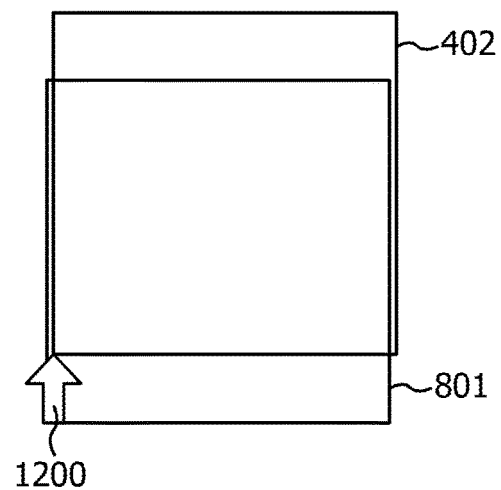

FIG. 12B illustrates a manner in which an image for which local positioning has been performed is extracted from a comparison destination CT image by performing a conversion process by parallel translation using the representative vector 1200. As depicted in FIG. 12B, the second registration unit 142 can determine the corresponding region 402 by parallelly translating the region 801 in the comparison destination CT corresponding to the given region 401 of the comparison source CT image in response to the representative vector 1200. Further, by extracting an image of the corresponding region 402 from the comparison destination CT image, the second registration unit 142 can extract an image for which local positioning has been performed.

Meanwhile, FIG. 13 depict views illustrating a calculation method of a representative vector when it is decided that a convergence region does not exist. If the convergence region 702 is not included in the representative vector calculation target region 800, then the representative vector calculation unit 1004 determines a representative vector using the corresponding vectors calculated by the representative vector calculation target region 800. However, the corresponding vectors included in the tumor region 703 are excluded. It is to be noted that, since a corresponding point to a feature point does not exist in the tumor region 703, no corresponding vector exists, and therefore, the calculated representative vector is same irrespective of whether or not corresponding vectors existing in the tumor region 703 are excluded.

Figure 13A:
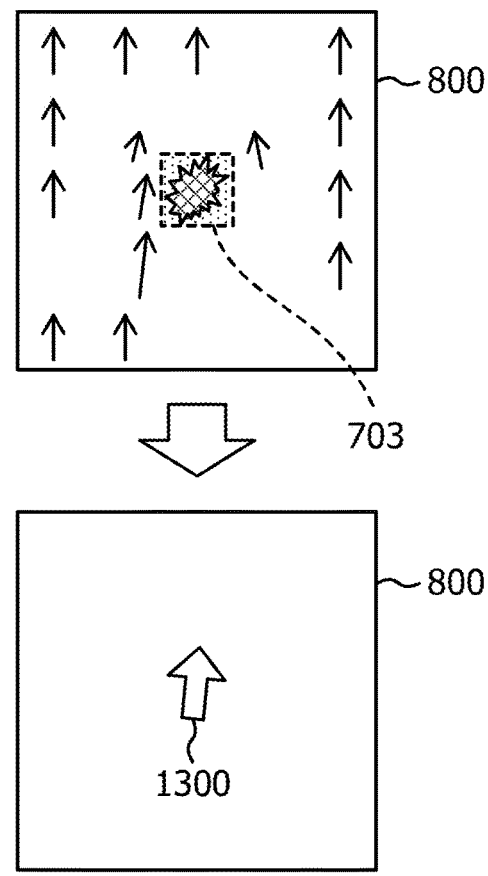
FIGS. 13A and 13B depict views illustrating a calculation method of a representative vector when it is decided that there is no convergence region.

In the example of FIG. 13A, 15 corresponding vectors (indicated by dark arrow marks) are calculated in the representative vector calculation target region 800, and the representative vector calculation unit 1004 calculates a representative vector using the 15 corresponding vectors. A representative vector 1300 indicates a representative vector calculated using the 15 corresponding vectors. In this manner, when the convergence region 702 is not included in the representative vector calculation target region 800, since there is no influence of non-rigid deformation, a representative vector can be calculated using all corresponding vectors.

Figure 13B:
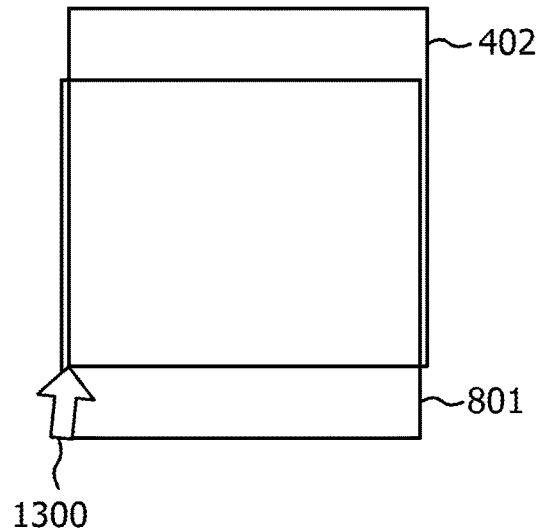

FIG. 13B illustrates a manner in which an image for which local positioning has been performed is extracted from the comparison destination CT image by performing a conversion process by parallel translation using the representative vector 1300. As illustrated in FIG. 13B, the second registration unit 142 can determine the corresponding region 402 by parallelly translating the region 801 in the comparison destination CT image corresponding to the given region 401 of the comparison source CT image in response to the representative vector 1300. Further, the second registration unit 142 can extract an image for which local positioning has been performed by extracting an image of the corresponding region 402 from the comparison destination CT image.

Figure 14:
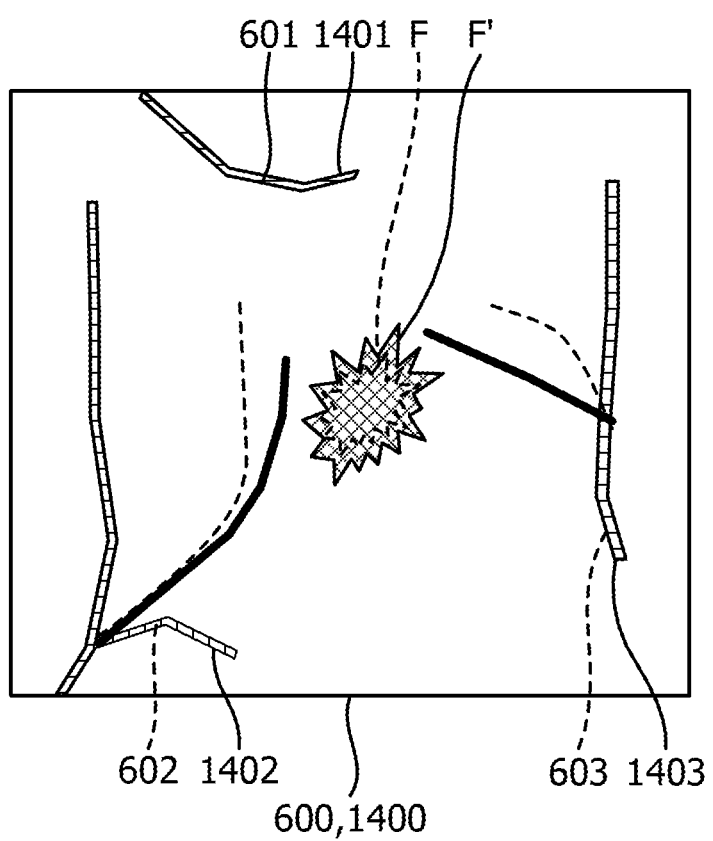
FIG. 14 is a view depicting an image obtained by performing local positioning using a representative vector from which an influence of non-rigid deformation has been removed.

Here, an image obtained by the positioning unit 1005 performing local positioning using the representative vector 1200 that is free from an influence of non-rigid deformation is described. FIG. 14 is a view depicting an image obtained by performing local positioning using a representative vector from which an influence of non-rigid deformation has been removed.

It is to be noted that, in the example of FIG. 14, an image 1400 of the corresponding region 402 obtained by the positioning unit 1005 performing local positioning using the representative vector 1200 from which the influence of non-rigid deformation has been excluded and the image 600 of the given region 401 of the comparison source CT image are depicted in an overlapping relationship with each other.

As depicted in FIG. 14, the positions of blood vessels 1401 to 1403 and the tumor F' included in the image 1400 are substantially same as the blood vessels 601 to 603 and the tumor F included in the image 600, respectively. In other words, in the image 1400, the fluctuation of the positions based on the breathing and the heart beating is cancelled. Meanwhile, the blood vessels 1402 and 1403 which are positioned around the tumor F' are displaced in position from the blood vessels 601 to 603 included in the image 600 which are positioned around the tumor F. In other words, in the image 1400, the influence of the fluctuation of the positions based on the tumor remains.

Now, a particular example of the function of the image processor 1006 that performs an image processing process for an image of the corresponding region 402 obtained by the positioning unit 1005 performing local positioning is described. FIG. 15 depict views illustrating a particular example of an image processing process executed by an image processor. FIG. 15A illustrates a manner in which a change of a tissue based on a change of a tumor is visualized by the image processor 1006 calculating a difference between pixel values of an image 600 of a given region 401 and an image 1400 of a corresponding region 402.

As depicted in FIG. 15A, the tumor included in the image 1400 of the corresponding region 402 is greater than the tumor included in the image 600 of the given region 401, and a cavity is generated in the inside of the tumor because of disappearance of a tissue.

The image processor 1006 calculates differences between pixel values of pixels of the image 600 of the given region 401 and pixel values of pixels of the image 1400 of the corresponding region 402 to generate a difference image 1510 thereby to visualize a variation between the image 600 and the image 1400.

For example, the image processor 1006 decides pixels whose difference value is in the positive and is greater than a given threshold value from among the pixels of the difference image 1510 as pixels indicative of a tumor having appeared newly and colors the pixels, for example, in red. Further, the image processor 1006 determines pixels whose difference value is in the negative and is smaller than a given threshold value from among the pixels of the difference image 1510 as pixels indicative of a disappeared tissue and colors the pixels, for example, in blue. It is to be noted that, from among the pixels of the difference image 1510, those pixels the absolute value of the difference value of which is equal to or lower than the given threshold value are decided as pixels having no change, and change in color is not performed for the pixels.

Consequently, if a health care worker observes the difference image 1510, then the health care worker can recognize a change of a tissue based on a change of the tumor (appearance, disappearance, or no change) readily.

FIGS. 15B-1 and 15B-2 illustrate a manner in which a moving direction and a movement amount of a tissue based on a change of the tumor are visualized by the image processor 1006 displaying vectors indicative of fluctuations of the position based on a change of the tumor.

Particularly, FIG. 15B-1 illustrates a manner in which the image processor 1006 acquires difference vectors calculated by the convergence region decision unit 1003 (for example, difference vectors illustrated in FIG. 11) and displays the difference vectors on a translucent layer superposed on the image 1400. By displaying the difference vectors in an overlapping relationship with the image 1400 through the translucent layer in this manner, the health care worker can easily recognize the moving direction and the movement amount of the tumor based on the change of the tumor.

Meanwhile, FIG. 15B-2 illustrates a manner in which the image processor 1006 acquires difference vectors calculated by the convergence region decision unit 1003 and superposes a translucent layer, which is colored at corresponding positions of the partition group 1102, on the image 1400. It is to be noted that the image processor 1006 colors the translucent layer at positions of the partition group 1102 corresponding to the difference vectors with shading corresponding to the magnitudes of the difference vectors. For example, as the magnitude of the difference vector increases, the partition at the corresponding position is colored in a more saturated color, and as the magnitude of the difference vector decreases, the partition at the corresponding position is colored in a less saturated color.

Consequently, the health care worker can recognize that, at the position of a colored partition, movement of a tissue has occurred on the basis of a change of a tumor. Further, the health care worker can recognize the magnitude of the movement amount of the tissue based on the change of the tumor on the basis of the saturation of the color.

FIGS. 15C-1 and 15C-2 illustrate a manner in which a tendency of a change of a tissue based on a change of a tumor is visualized by the image processor 1006 on the basis of a distribution of difference vectors acquired from the convergence region decision unit 1003. It is illustrated in a manner in which the image processor 1006 calculates the number per unit area of difference vectors acquired from the convergence region decision unit 1003 and superposes a translucent layer colored in a region corresponding to a convergence region with saturation in accordance with the calculated number of difference vectors on an image 1400.

Consequently, the health care worker can recognize a tendency of a change of the tissue based on a change of the tumor (whether the number of tissues whose positions have been changed by a great amount is great or small) on the basis of the saturation of the applied color. FIG. 15C-1 illustrates a manner in which a region corresponding to the convergence region 702 is colored in a more saturated color because the number of difference vectors per unit area is great in the region compared with FIG. 15C-2.

With the displays depicted in FIGS. 15C-1 and 15C-2, it can be recognized readily at which location difference vectors are concentrated although, if difference vectors are merely displayed in such a case that a plurality of regions that may possibly suffer from adenocarcinoma exist in the proximity of each other, then it is less likely to recognize at which location the difference vectors are concentrated.

Figure 16:
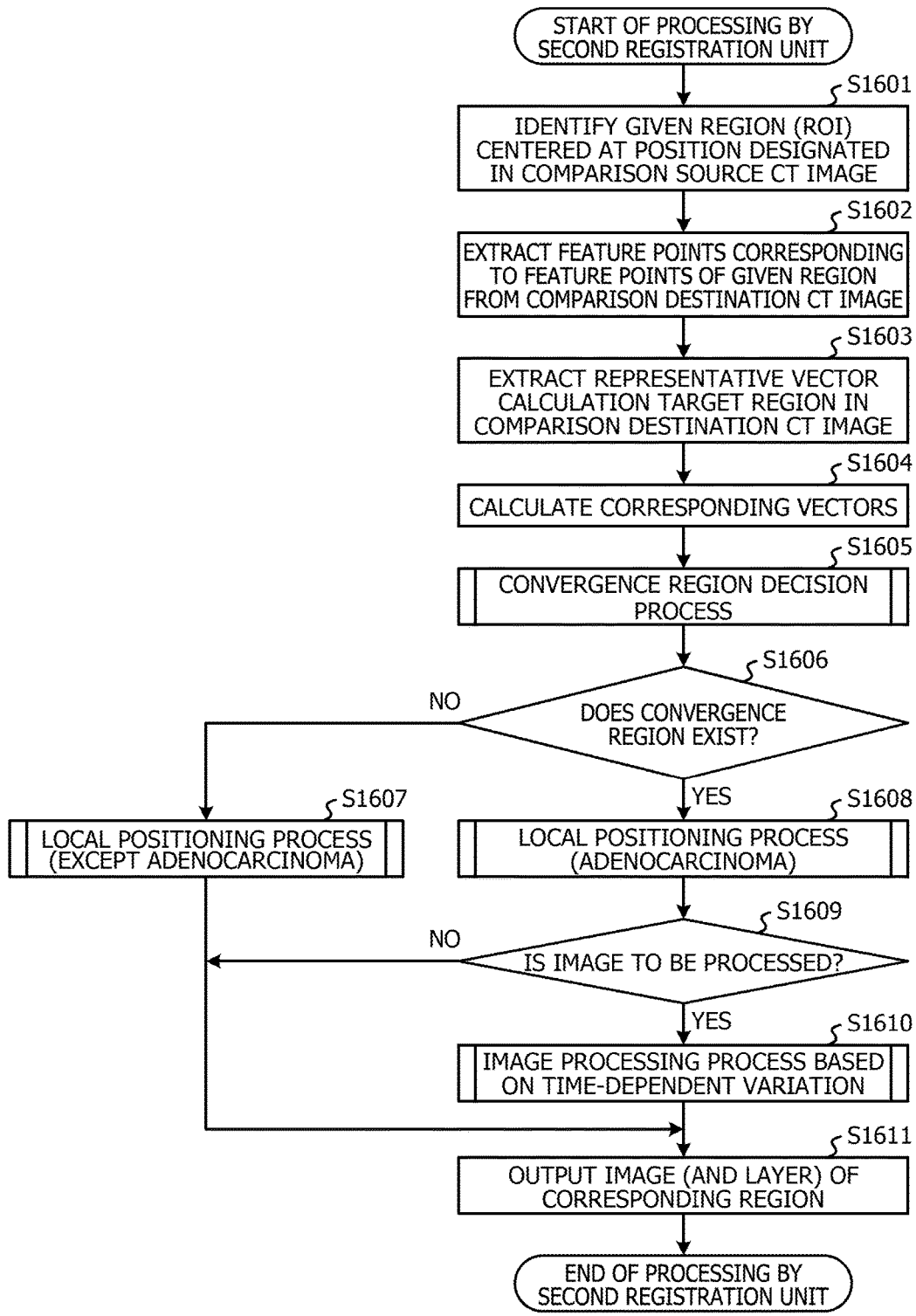
FIG. 16 is a first flow chart illustrating a process executed by a second registration unit.

Now, a flow of processing executed by the second registration unit 142 is described. FIG. 16 is a first flow chart of processing executed by a second registration unit.

At step S1601, the region identification unit 1001 identifies a given region (ROI) 401 centered at the position of a tumor F designated by a health care worker on a comparison source CT image.

At step S1602, the corresponding vector calculation unit 1002 extracts feature points from the given region 401 of the comparison source CT image identified by the region identification unit 1001. Further, the corresponding vector calculation unit 1002 searches for feature points in a comparison destination CT image corresponding to the extracted feature points.

At step S1603, the convergence region decision unit 1003 extracts a region including the feature points searched out from the comparison destination CT image as a representative vector calculation target region 800.

At step S1604, the corresponding vector calculation unit 1002 calculates corresponding vectors on the basis of the differences between the positions of the feature points extracted from the comparison source CT image and the positions of the feature points in the comparison destination CT image corresponding to the feature points.

At step S1605, the convergence region decision unit 1003 decides on the basis of calculated corresponding vectors whether or not a convergence region 702 is included in the representative vector calculation target region 800. If it is decided that a convergence region 702 is included, then the convergence region decision unit 1003 calculates a boundary position between the normal region 701 and the convergence region 702. It is to be noted that a detailed flow chart of the convergence region decision process at step S1605 is hereinafter described.

At step S1606, the representative vector calculation unit 1004 decides whether or not a convergence region 702 is included on the basis of a result of the convergence region decision process (step S1605). If it is decided at step S1606 that a convergence region 702 is not included, then the processing advances to step S1607. At step S1607, the representative vector calculation unit 1004 and the positioning unit 1005 perform a local positioning process for a tumor other than adenocarcinoma.

On the other hand, if it is decided at step S1606 that a convergence region 702 is included, then the processing advances to step S1608. At step S1608, the representative vector calculation unit 1004 and the positioning unit 1005 perform a local positioning process for adenocarcinoma.

It is to be noted that a detailed flow chart of the local positioning process at steps S1607 and S1608 is hereinafter described.

At step S1609, the image processor 1006 decides whether or not an instruction to perform image processing has been accepted from a health care worker. If an instruction to perform image processing has not been accepted, then the processing advances to step S1611. In this case, at step S1611, an image of the corresponding region 402 obtained by the local positioning process performed at step S1607 or step S1608 is outputted to the display controller 143. As a result, the display controller 143 causes an image of the corresponding region 402 obtained by the local positioning process performed at step S1607 or step S1608 (image for which image processing has not been performed) to be displayed in an enlarged scale on an enlarged display screen image.

On the other hand, if it is decided at step S1609 that an instruction to perform image processing has been accepted, then the processing advances to step S1610. At step S1610, the image processor 1006 performs an image processing process based on a time-dependent variation. Thereafter, the processing advances to step S1611.

In this case, at step S1611, an image (including a translucent layer) obtained by performing the image processing process (step S1610) for the image of the corresponding region 402 obtained by performing the local positioning process (step S1608) is outputted to the display controller 143. As a result, the display controller 143 causes the image (including the translucent layer) obtained by performing the image processing process for the image obtained by the local positioning process performed at step S1608 to be displayed in an enlarged scale on the enlarged display screen image. It is to be noted that a detailed flow chart of the image processing process based on a time-dependent variation at step S1610 is hereinafter described.

Figure 17:
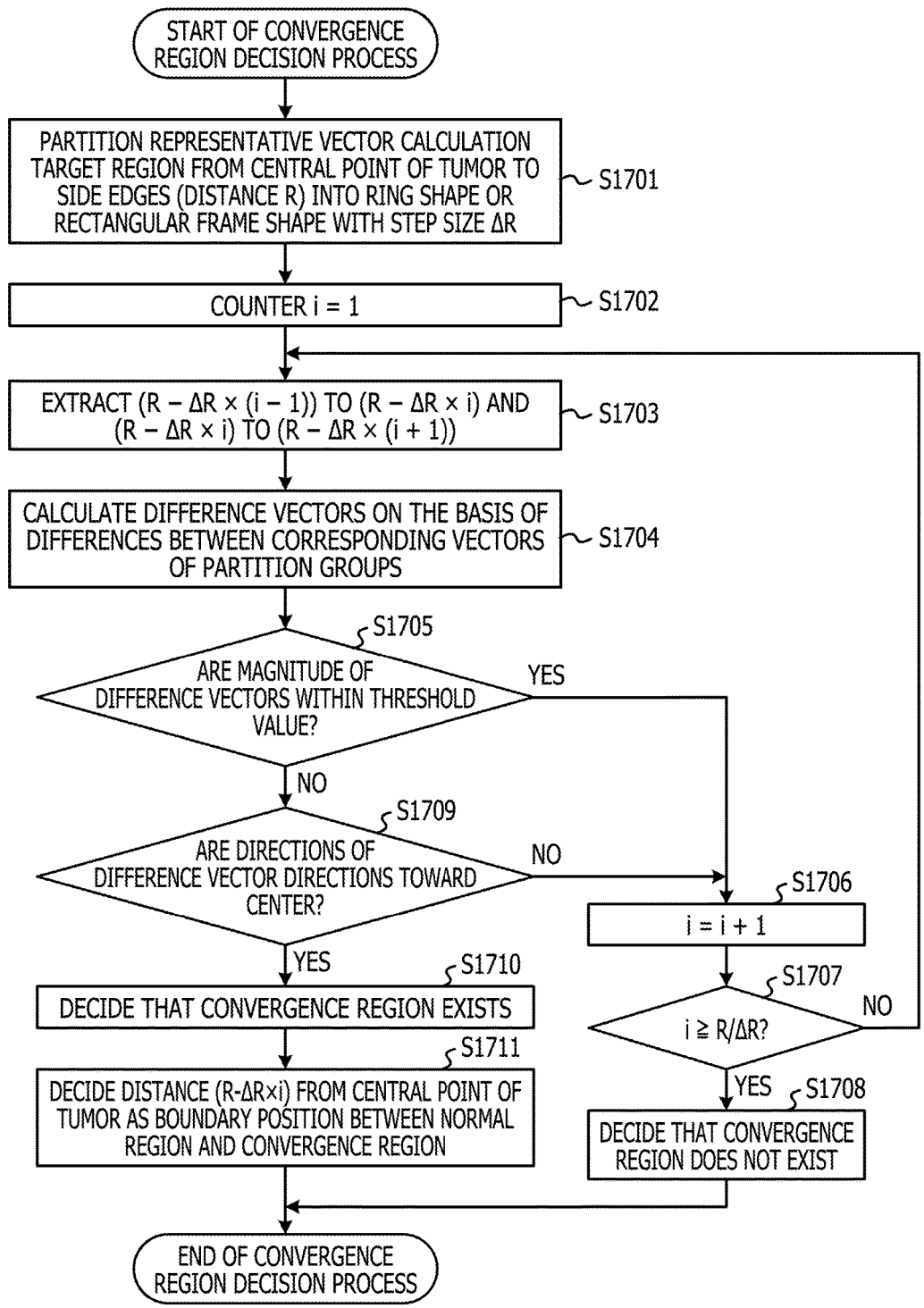
FIG. 17 is a flow chart of a convergence region decision process.

Now, details of the convergence region decision process (step S1605) are described. FIG. 17 is a flow chart of a convergence region decision process.

At step S1701, the convergence region decision unit 1003 partitions the representative vector calculation target region 800 from the center (tumor central point O) to the side edges into ring shapes or rectangular frame shapes with a step size ΔR. At step S1702, the convergence region decision unit 1003 substitutes 1 into a counter i.

At step S1703, the convergence region decision unit 1003 extracts a partition group in a range of (R−ΔR×(i−1)) to (R−ΔR×i) and a partition group within a range of (R−ΔR×i) to (R−ΔR×(i+1)) positioned at the inner side (side nearer to the tumor) of the partition group.

At step S1704, the convergence region decision unit 1003 calculates a difference between each adjacent ones of the corresponding vectors existing in the extracted partition groups to determine difference vectors.

At step S1705, the convergence region decision unit 1003 decides whether or not the magnitude of each difference vector is within a threshold value. If it is decided at step S1705 that the magnitude of the difference vector is within the threshold value, then the processing advances to step S1706, at which the counter i is incremented.

At step S1707, the convergence region decision unit 1003 decides whether or not i≥R/ΔR is satisfied. If it is decided that the inequality is not satisfied, then the convergence region decision unit 1003 decides that a partition group exists at the further inner side (side nearer to the tumor). Then, the processing returns to step S1703.

On the other hand, if it is decided at step S1707 that i≥R/ΔR is satisfied, then the convergence region decision unit 1003 decides that a difference vector has been calculated with regard to all partition groups. Then, the processing advances to step S1708.

At step S1708, the convergence region decision unit 1003 decides that a convergence region 702 is not included in the representative vector calculation target region 800 and ends the convergence region decision process.

On the other hand, if it is decided at step S1705 that the magnitude of the difference vector is greater than the threshold value, then the processing advances to step S1709. At step S1709, the convergence region decision unit 1003 decides whether or not it can be regarded that the direction of the difference vector is directed toward the center of the representative vector calculation target region 800.

If it is decided at step S1709 that it is difficult to regard that the direction of the difference vector is directed toward the center, then the processing advances to step S1706. On the other hand, if it is decided at step S1709 that it can be regarded that the direction of the difference vector is directed toward the center, then the processing advances to step S1710.

At step S1710, the convergence region decision unit 1003 decides that a convergence region 702 is included in the representative vector calculation target region 800, and the processing advances to step S1711. At step S1711, the convergence region decision unit 1003 decides that the position at which the distance from the center of the representative vector calculation target region 800 is equal to (R−ΔR×i) is a boundary position between the normal region 701 and the convergence region 702, thereby ending the convergence region decision process.

Now, details of the local positioning process (steps S1607 and S1608) are described. FIG. 18 depict flow charts of a local positioning process.

Figure 18A:
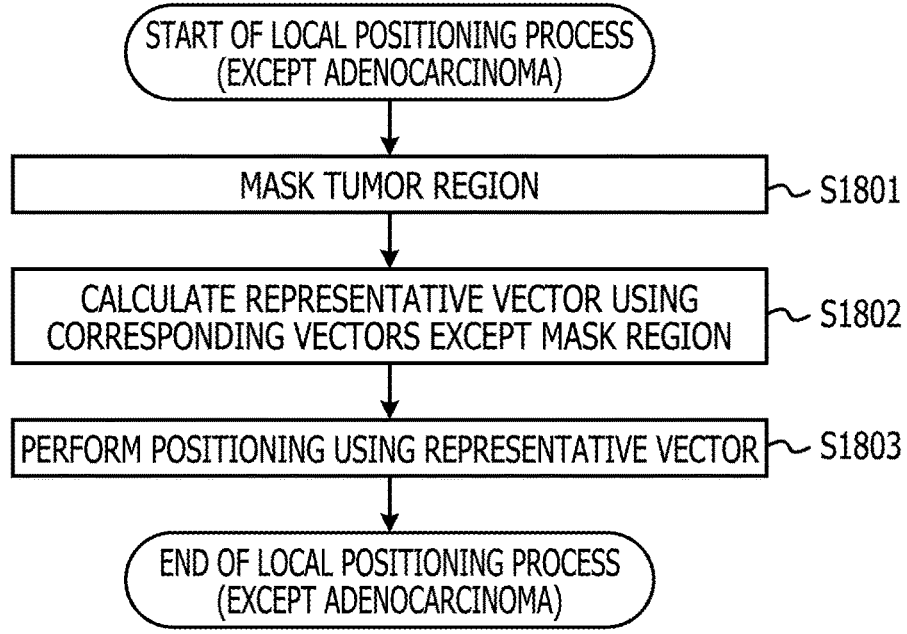
FIGS. 18A and 18B depict flow charts of a local positioning process.

In particular, FIG. 18A is a flow chart of the local positioning process (for other than adenocarcinoma). At step S1801, the representative vector calculation unit 1004 masks the tumor region 703 from within the representative vector calculation target region 800.

At step S1802, the representative vector calculation unit 1004 calculates a representative vector using the corresponding vectors in the region other than the tumor region 703 masked at step S1801 from among the corresponding vectors included in the representative vector calculation target region 800.

At step S1803, the positioning unit 1005 extracts an image of the corresponding region 402 corresponding to the given region 401 from the comparison destination CT image using the calculated representative vector. Consequently, an image for which local positing has been performed can be extracted.

Figure 18B:
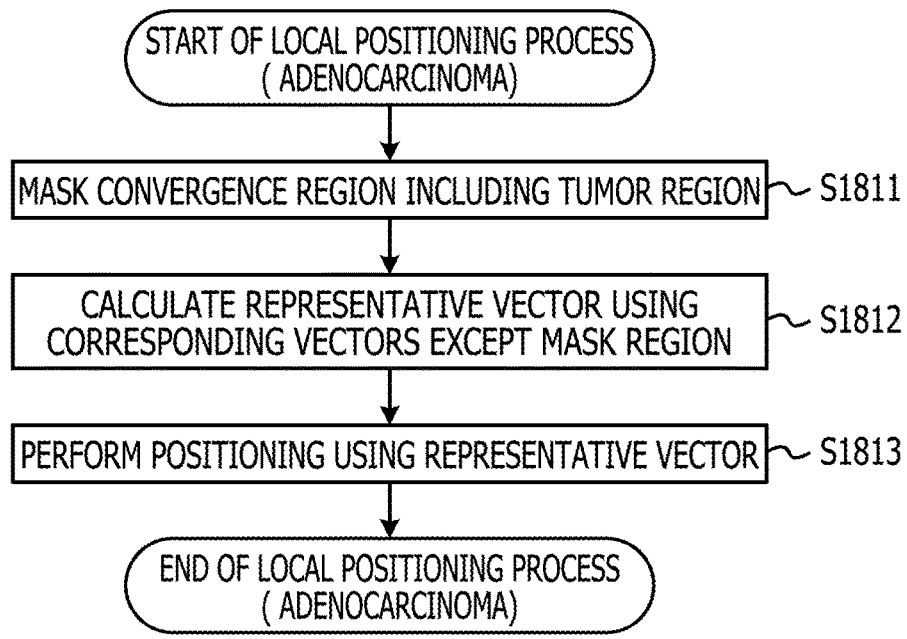

Meanwhile, FIG. 18B is a flow chart of local positioning (for adenocarcinoma). At step S1811, the representative vector calculation unit 1004 masks the convergence region 702 including the tumor region 703 from within the representative vector calculation target region 800.

At step S1812, the representative vector calculation unit 1004 calculates a representative vector using the corresponding vectors in the region other than the convergence region 702 masked at step S1811 from among the corresponding vectors included in the representative vector calculation target region 800.

At step S1813, the positioning unit 1005 extracts the image 1400 of the corresponding region 402 corresponding to the given region 401 from the comparison destination CT image using the calculated representative vector. Consequently, an image for which local positioning has been performed can be extracted.

In this manner, if the second registration unit 142 in the present embodiment decides that the magnitude of a difference vector is within the threshold value and the region in question is a normal region 701, then the second registration unit 142 calculates a representative vector using the corresponding vectors of the partitions. Further, if it is decided that the convergence region 702 is included according to the difference vectors have a magnitude greater than the threshold value and beside are directed toward the center, the second registration unit 142 calculates a representative vector using corresponding vectors in which the partition is far from the tumor compared with the partition of the convergence region 702. In other words, the second registration unit 142 calculates a representative vector using corresponding vectors of the feature points in positions spaced by equal to or more than the threshold value from the tumor region. Consequently, since a representative vector can be calculated excluding the influence of non-rigid deformation, the accuracy in local positioning can be raised.

Now, a flow of processing when the image processing process (step S1610) based on a time-dependent variation is performed for the image 1400 of the corresponding region 402 obtained by the local positioning performed as described above is described in detail.

Figure 19:
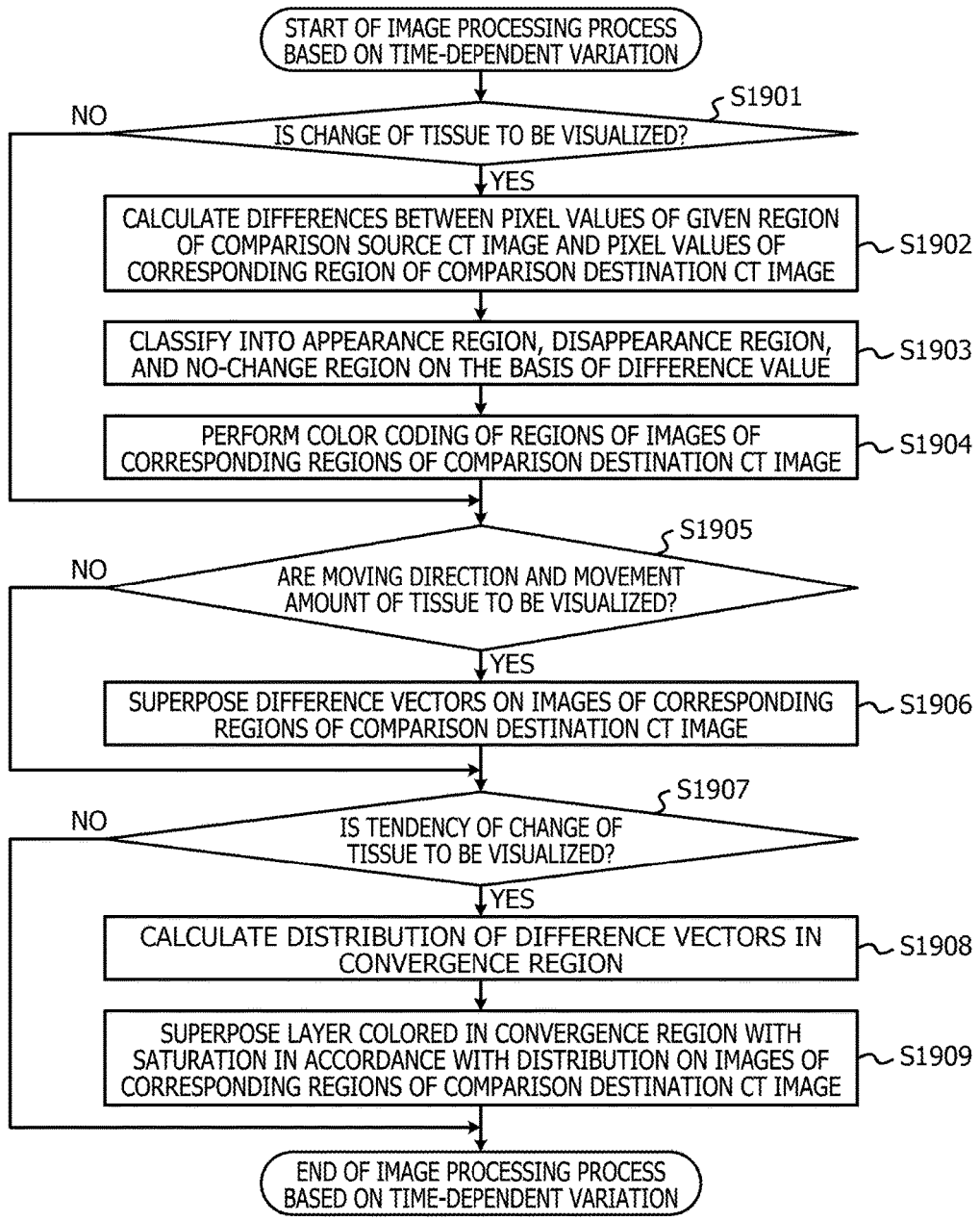
FIG. 19 is a flow chart of an image processing process based on a time-dependent variation.

FIG. 19 is a flow chart of an image processing process based on a time-dependent variation. At step S1901, the image processor 1006 decides whether or not image processing for visualizing a change of a tissue is to be performed. On a parallel display screen image 300, a health care worker can perform an operation (first operation) for instructing to perform image processing for visualizing a change of a tissue through the operation unit 207. Therefore, the image processor 1006 decides whether or not a first operation has been performed by a health care worker to determine whether or not image processing for visualizing a change of a tissue is to be performed.

If it is decided that a first operation has not been performed by a health care worker, then the image processor 1006 advances the processing to step S1905. On the other hand, if it is decided that a first operation has been performed by a health care worker, then the image processor 1006 advances the processing to step S1902.

At step S1902, the image processor 1006 calculates a difference value between each pixel value of the image 600 of the given region 401 of the comparison source CT image and a corresponding pixel value of the image 1400 of the corresponding region 402 of the comparison destination CT image to generate a difference image 1510.

At step S1903, the image processor 1006 classifies the difference image 1510 into an appearance region, a disappearance region, or a no-change region on the basis of the difference values of the pixels included in the generated difference image 1510.

At step S1904, the image processor 1006 performs color conversion for the image 1400 of the corresponding region 402 of the comparison destination CT image on the basis of a result of the classification at step S1903. For example, the image processor 1006 converts pixels corresponding to an appearance region of the image 1400 of the corresponding region 402 of the comparison destination CT image into those of a given color (for example, red). Further, the image processor 1006 converts pixels corresponding to a disappearance region of the image 1400 of the corresponding region 402 of the comparison destination CT image into those of another given color (for example, blue).

At step S1905, the image processor 1006 determines whether or not image processing for visualizing a moving direction and a movement amount of a tissue is to be performed. A health care worker can perform, on the parallel display screen image 300, an operation (second operation) for instructing to perform image processing for visualizing the moving direction and the movement amount of a tissue through the operation unit 207. Therefore, the image processor 1006 decides whether or not a second operation has been performed by a health care worker to determine whether or not image processing for visualizing the moving direction and the movement amount of a tissue is to be performed.

If it is decided that a second operation has not been performed by a health care worker, then the image processor 1006 advances the processing to step S1907. On the other hand, if it is decided that a second operation has been performed by a health care worker, then the image processor 1006 advances the processing to step S1906.

At step S1906, the image processor 1006 acquires difference vectors calculated by the convergence region decision unit 1003. Further, the image processor 1006 causes an image of the acquired difference vectors to be displayed on a translucent layer to be superposed on the image 1400 of the corresponding region 402. Further, the image processor 1006 superposes a translucent layer, on which the difference vectors are displayed, on the image 1400 of the corresponding region 402.

At step S1907, the image processor 1006 determines whether or not image processing for visualizing a tendency of a change of a tissue is to be performed. A health care worker can perform an operation (third operation) for instructing to perform image processing for visualizing a tendency of a change of a tissue on the parallel display screen image 300 through the operation unit 207. Therefore, the image processor 1006 decides whether or not a third operation has been performed by a health care worker to determine whether or not image processing for visualizing a tendency of a change of a tissue is to be performed.

If it is decided that a third operation has not been performed by a health care worker, then the image processor 1006 ends the image processing process based on a time-dependent variation. On the other hand, if it is decided that a third operation has been performed by a health care worker, then the image processor 1006 advances the processing to step S1908.

At step S1908, the image processor 1006 acquires the difference vectors calculated by the convergence region decision unit 1003. Further, the image processor 1006 calculates the number of acquired difference vectors per unit area and determines saturation in accordance with the calculated number.

At step S1909, the image processor 1006 colors a region corresponding to the convergence region on the translucent layer to be superposed on the image 1400 of the corresponding region 402 with a given color based on the determined saturation. Further, the image processor 1006 superposes a translucent layer colored in the region thereof corresponding to the convergence region. Further, the image processor 1006 superposes the translucent layer colored in the region thereof corresponding to the convergence region on the image 1400 of the corresponding region 402.

As apparent from the description given above, in the present embodiment, if an image of a given region including a tumor in a comparison source CT image is designated, then a conversion process by parallel translation is performed in the comparison destination CT image using corresponding vectors spaced from the convergence region to extract an image of the corresponding region. Consequently, local positioning of high accuracy from which an influence of non-rigid deformation (a fluctuation amount of the position based on a change of the tumor (time-dependent variation)) is removed can be performed.

Further, in the present embodiment, image processing for visualizing a fluctuation amount of the position based on a time-dependent variation of a tumor is performed for an image of a corresponding region obtained by performing local positioning.

Consequently, even in a case in which an image is deformed by an influence of the breathing or the heart beating, a health care worker can easily decide a location converged by an influence of the alveoli collapsed by the tumor. As a result, the load when a health care worker makes a decision from the comparison destination CT image can be reduced.

Second Embodiment

The second registration unit in the first embodiment described above determines a given region 401 in response to designation of the position of a tumor F on a comparison source CT image by a health care worker. In contrast, a second registration unit in the second embodiment scans a comparison source CT image successively for regions of a given size as ROI candidates with a given scanning width and executes a convergence region decision process at each of the scanning positions. Further, the second registration unit in the second embodiment determines an ROI candidate at a position at which it is decided that a convergence region exists as a given region (ROI) 401. In this manner, in the second embodiment, since a given region (ROI) 401 is determined on the basis of a result of decision regarding whether or not there exists a convergence region, a health care worker may not perform a process for designating a tumor F on a comparison source CT image. As a result, the load on the health care worker upon diagnosis can be reduced. In the following, the second embodiment is described principally in connection with differences thereof from the first embodiment described hereinabove.

Figure 20:
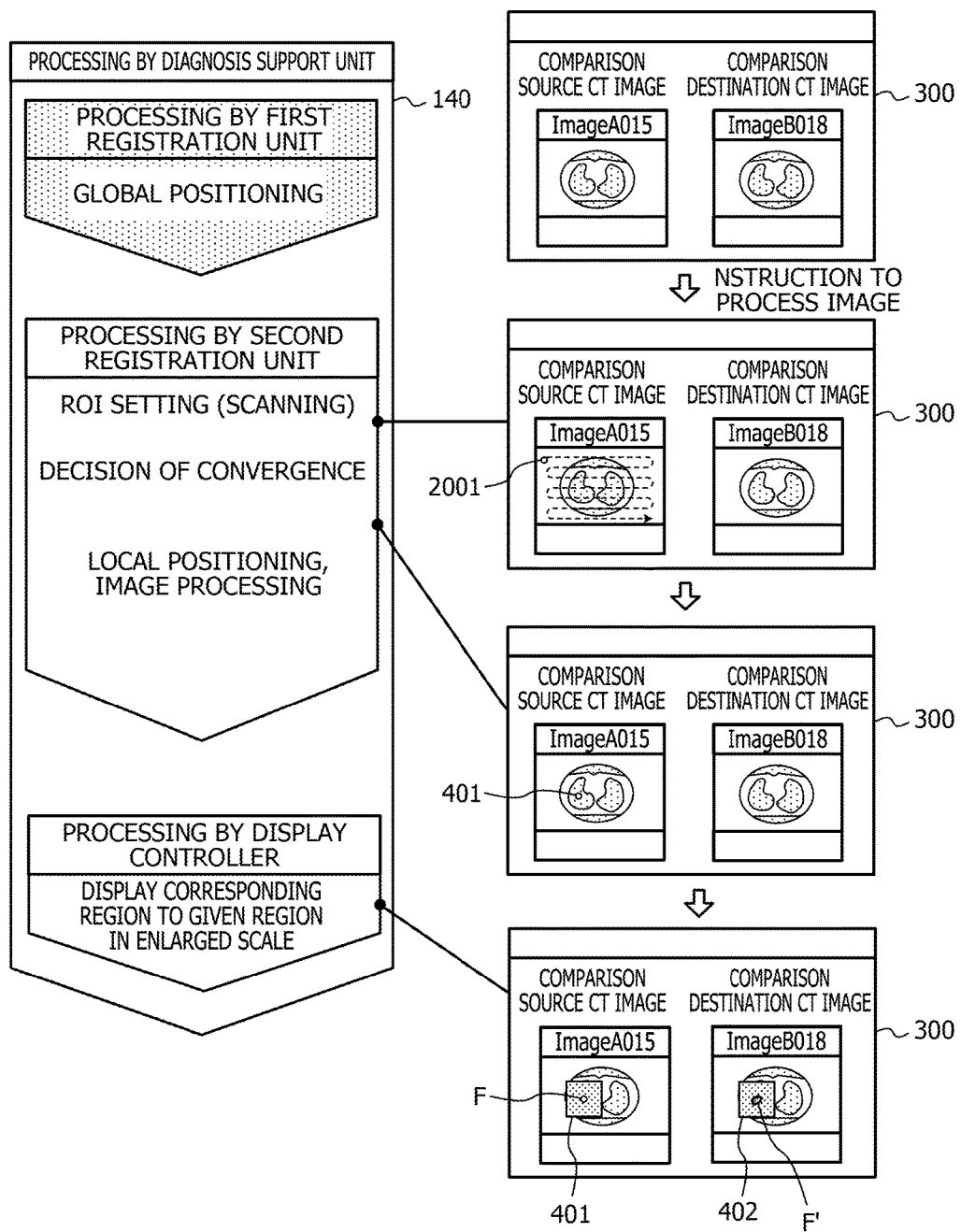
FIG. 20 is a second view illustrating a relationship among process contents of a diagnosis support unit of an image processing apparatus, operation contents of a health care worker, and display contents of a parallel display screen image.

FIG. 20 is a view illustrating a relationship between processing contents of a diagnosis supporting unit, operation contents of a health care worker, and display contents of a parallel display screen image in an image processing apparatus. FIG. 20 corresponds to FIG. 4 (view depicting processing contents and so forth after global positioning) depicted in connection with the first embodiment.

As depicted in FIG. 20, when global positioning is completed, the second registration unit 142 accepts an instruction regarding whether or not image processing is to be performed from a health care worker. Further, the second registration unit 142 scans the comparison source CT image for ROI candidates 2001 of a given size with a given scanning width and executes a convergence region decision process (step S1605) at each of the scanning positions. Then, the second registration unit 142 determines a region to be specified by the ROI candidate 2001 at a position at which it has been decided that there exists a convergence region as a given region (ROI) 401.

After the given region (ROI) 401 is determined, the second registration unit 142 performs a local positioning process (step S1608) for the comparison destination CT image on the basis of an image of the determined given region (ROI) 401. Consequently, the second registration unit 142 extracts an image of the corresponding region 402 including the position of a tumor F' corresponding to the tumor F (image for which local positioning has been performed).

Further, the second registration unit 142 performs an image processing process (step S1610) based on a time-dependent variation for the image of the corresponding region 402 obtained by performing the local positioning. Further, the second registration unit 142 notifies the display controller 143 of the image of the given region (ROI) 401 determined in the comparison source CT image and an image of the corresponding region 402 extracted from the comparison destination CT image (where the image has been processed, the image after the processing).

The display controller 143 causes the image of the given region (ROI) 401 notified from the second registration unit 142 to be displayed in an enlarged scale on the enlarged display screen image on the comparison source CT image. Further, the display controller 143 causes the image of the corresponding region 402 notified from the second registration unit 142 to be displayed in an enlarged scale on the enlarged display screen image of the comparison destination CT image. Consequently, the image for which the image processing has been performed is displayed on the image of the corresponding region 402 obtained by performing local positioning.

Figure 21:
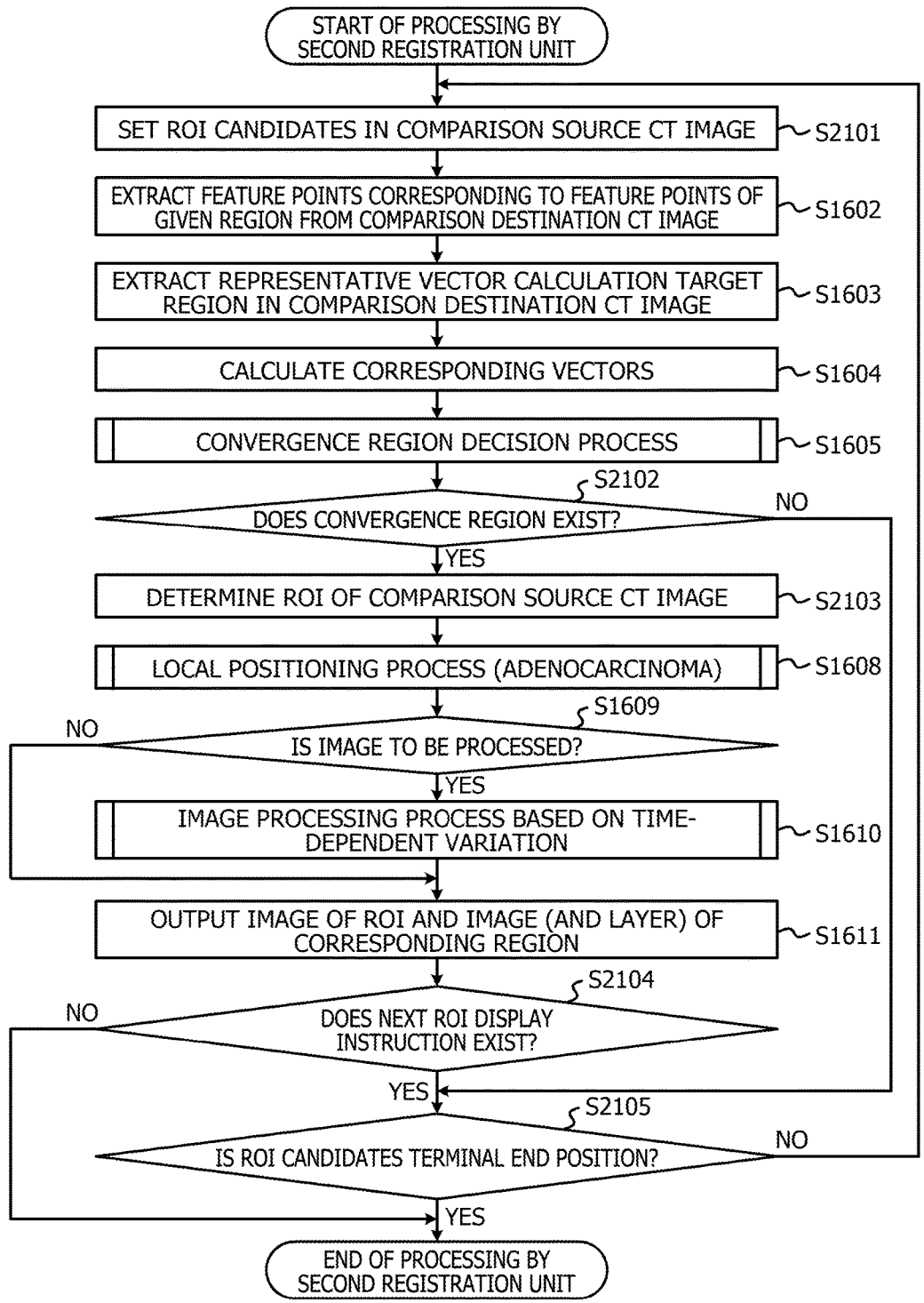
FIG. 21 is a second flow chart of a process executed by a second registration unit.

Now, a flow of processing by the second registration unit 142 in the second embodiment is described. FIG. 21 is a second flow chart of processing executed by a second registration unit. It is to be noted that, from among steps included in the flow chart depicted in FIG. 21, like steps to the steps included in the flow chart of the first embodiment described hereinabove with reference to FIG. 16 are denoted by like reference characters and overlapping description of these steps is omitted herein.

At step S2101, the region identification unit 1001 reads out an ROI candidate 2001 of a size determined in advance and sets the ROI candidate 2001 to a given position of a comparison source CT image. Here, the region identification unit 1001 sets the ROI candidate 2001 to a scanning starting position of the comparison source CT image (left upper corner position of the comparison source CT image).

At steps S1602 to S1605, it is decided whether or not there exists a convergence region on the basis of an image of a region specified by the ROI candidate 2001 at the position set at step S2101.

If it is decided at step S2102 that there exists no convergence region as a result of the processes at steps S1602 to S1605, then the representative vector calculation unit 1004 advances the processing to step S2105.

At step S2105, the region identification unit 1001 decides whether or not the ROI candidate 2001 is positioned at a terminal end position of the comparison source CT image (right lower corner position of the comparison source CT image). If it is decided that there exists no terminal end position at step S2104, then the processing returns to step S2101.

In this case, the region identification unit 1001 sets the ROI candidate 2001 to a position moved by a given scanning width on the comparison source CT image. Then, the region identification unit 1001 executes the processes at steps S1601 to S1605.

In this manner, the second registration unit 142 in the present embodiment searches a given region (ROI) 401 by deciding whether or not there exists a convergence region while scanning an ROI candidate of a given size with a given scanning width on a comparison source CT image.

If it is decided that there exists a convergence region as a result of the processes at steps S1602 to S1605, then the representative vector calculation unit 1004 advances the processing from step S2102 to step S2103.

At step S2103, the region identification unit 1001 determines the ROI candidate 2001 at the position at which it is decided that there exists a convergence region as a given region (ROI) 401.

At step S1608, a local positioning process is performed on the basis of the image of the given region (ROI) 401 determined at step S2104. Further, if it is decided at step S1609 that an image processing process is to be performed, then an image processing process is performed at step S1610. Thereafter, the image of the given region (ROI) 401 and the image for which the image processing process has been performed in regard to the corresponding region (including the translucent layer) are outputted to the display controller 143. Thereafter, the processing advances to step S2104.

At step S2104, the region identification unit 1001 decides whether or not a displaying instruction for a next ROI is received from the display controller 143. It is to be noted that a health care worker can operate the operation unit 207 to issue an instruction on the parallel display screen image 300 to advance to a next ROI. If an operation for issuing an instruction to advance to a next ROI is performed by the health care worker, then the display controller 143 notifies the region identification unit 1001 of the instruction.

If it is decided at step S2104 that a displaying instruction of a next ROI is received, then the processing advances to step S2105. On the other hand, if it is decided that a displaying instruction of a next ROI is not received, then the processing by the second registration unit 142 is ended.

In this manner, the second registration unit 142 in the present embodiment scans a comparison source CT image with a given scanning width using ROI candidates of a given size. Then, the second registration unit 142 determines a region specified at a position at which it is decided that there exists a convergence region as a given region (ROI) and performs a local positioning process for the given region (ROI) on the basis of an image of the given region and then extracts an image of a corresponding region to perform an image processing process.

Consequently, a health care worker may not perform a process for designating a tumor F on a comparison source CT image, and the load on the health care worker upon diagnosis can be reduced.

Third Embodiment

The second registration unit in the second embodiment determines a given region (ROI) 401 by scanning an ROI candidate of a given size on a comparison source CT image with a given scanning width.

In contrast, a second registration unit in the third embodiment determines a given region (ROI) 401 while successively changing the size and the scanning width of an ROI candidate to be scanned on a comparison source CT image. It is to be noted that the second registration unit in the third embodiment determines, when it scans each ROI candidate with each scanning width, from among regions specified by positions at which it is decided that there exists a convergence region, a region in which, for example, the number of difference vectors is equal to or greater than a given threshold value as a given region (ROI) 401. In this manner, with the third embodiment, an optimum given region (ROI) can be determined by scanning while the size and the scanning width of an ROI candidate are successively changed. In the following, the third embodiment is described principally of differences thereof from the second embodiment described above.

Figure 22:
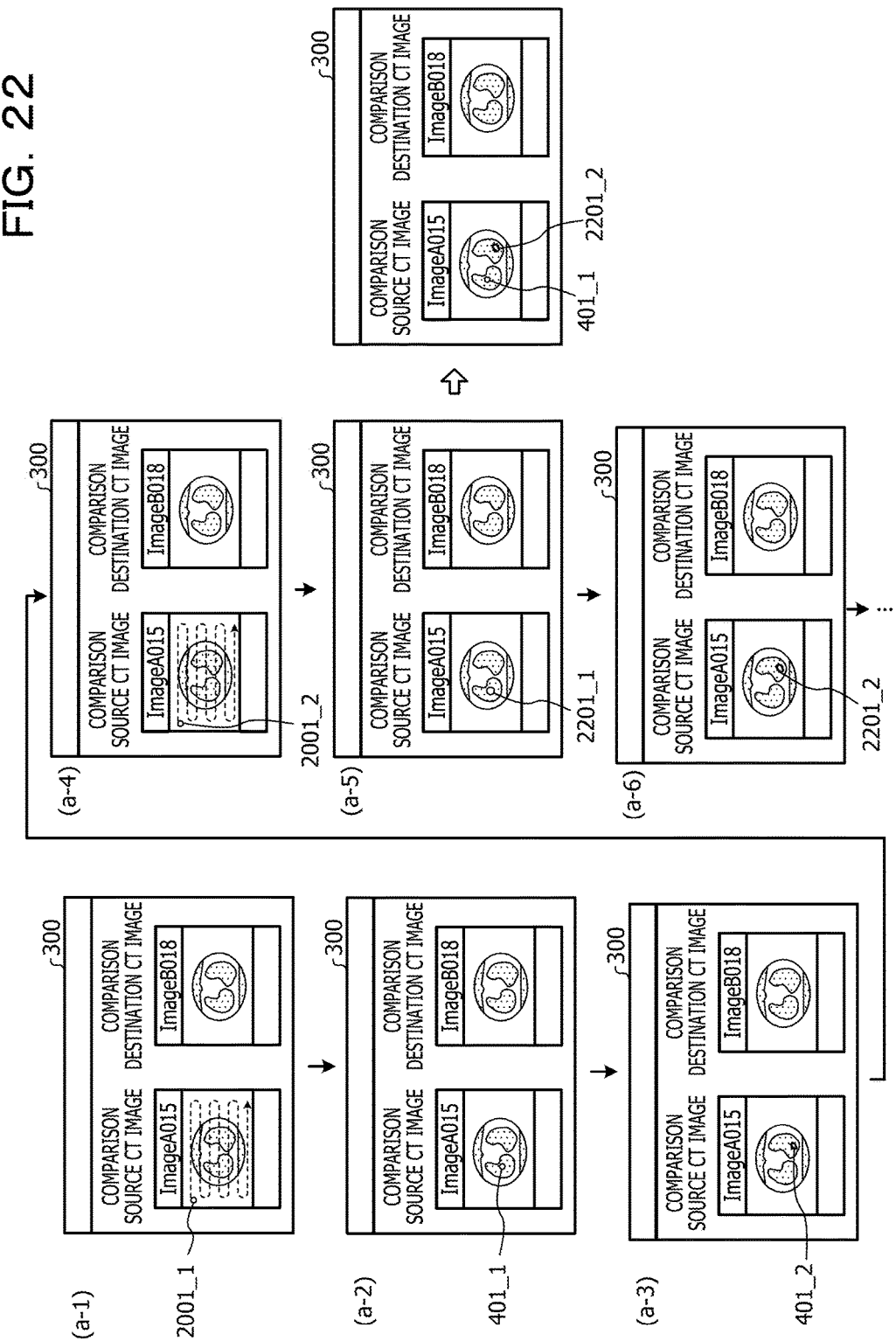
FIG. 22 depict views illustrating a process for scanning a comparison source CT image using region of interest (ROI) candidates to determine an ROI.

FIG. 22 depict views illustrating a process of scanning a comparison source CT image using ROI candidates to determine an ROI. FIG. 22A-1 illustrates a manner in which the second registration unit 142 scans ROI candidate 2001_1 of a comparison source CT image. It is to be noted that, in the present embodiment, the image processing apparatus 120 stores a plurality of ROI candidates in the auxiliary storage unit 204, and the second registration unit 142 successively reads out the ROI candidates and performs scanning of the ROI candidates on the comparison source CT image. FIG. 22A-1 indicates that the ROI candidate 2001_1 is read out first.

FIG. 22A-2 indicates that it is decided as a result of the scanning by the ROI candidate 2001_1 that a convergence region exists at a given position and a region specified by the position is decided as a given region (ROI) 401_1. Further, FIG. 22A-3 indicates that it is decided as a result of scanning of the ROI candidate 2001_1 that a convergence region exists at a position different from that of the given region 401_1 and a region specified by the position is decided as a given region (ROI) 401_2.

Meanwhile, FIG. 22A-4 indicates that, after scanning of the ROI candidate 2001_1 is completed, the second registration unit 142 reads out an ROI candidate 2001_2 of a size different from that of the ROI candidate 2001_1. The second registration unit 142 performs scanning of the comparison source CT image using the newly readout ROI candidate 2001_2.

FIG. 22A-5 indicates that it is decided as a result of the scanning of the ROI candidate 2001_2 that a convergence region exists at a given position and it is decided that a region specified by the position is a given region 2201_1. Further, FIG. 22A-6 indicates that it is decided as a result of scanning of the ROI candidate 2001_2 there exists a convergence region at a position different from that of the given region 2201_1 and a region specified by the position is decided as a given region 2201_2.

In this manner, by performing scanning of individual ROI candidates (2001_1, 2001_2, . . . ), a plurality of regions (401_1, 401_2, 2201_1, 2201_2, . . . ) are decided as given regions (ROIs). It is to be noted that, although, in the description of the example of FIG. 22, a change of the scanning width is not mentioned, when scanning of the ROI candidates (2001_1, 2001_2, . . . ) is performed, the scanning is performed changing the scanning width.

The second registration unit 142 determines a region that satisfies a given condition from among a plurality of regions (401_1, 401_2, 2201_1, 2201_2, . . . ) each decided as an ROI as an ROI.

The example of FIG. 22B illustrates a manner in which the given regions 401_1 and 2201_2 from among the plurality of regions (401_1, 401_2, 2201_1, 2201_2, ...) are determined as ROIs. Consequently, the second registration unit 142 in the present embodiment can determine a region of an optimum size at an optimum position as an ROI.

Figure 23:
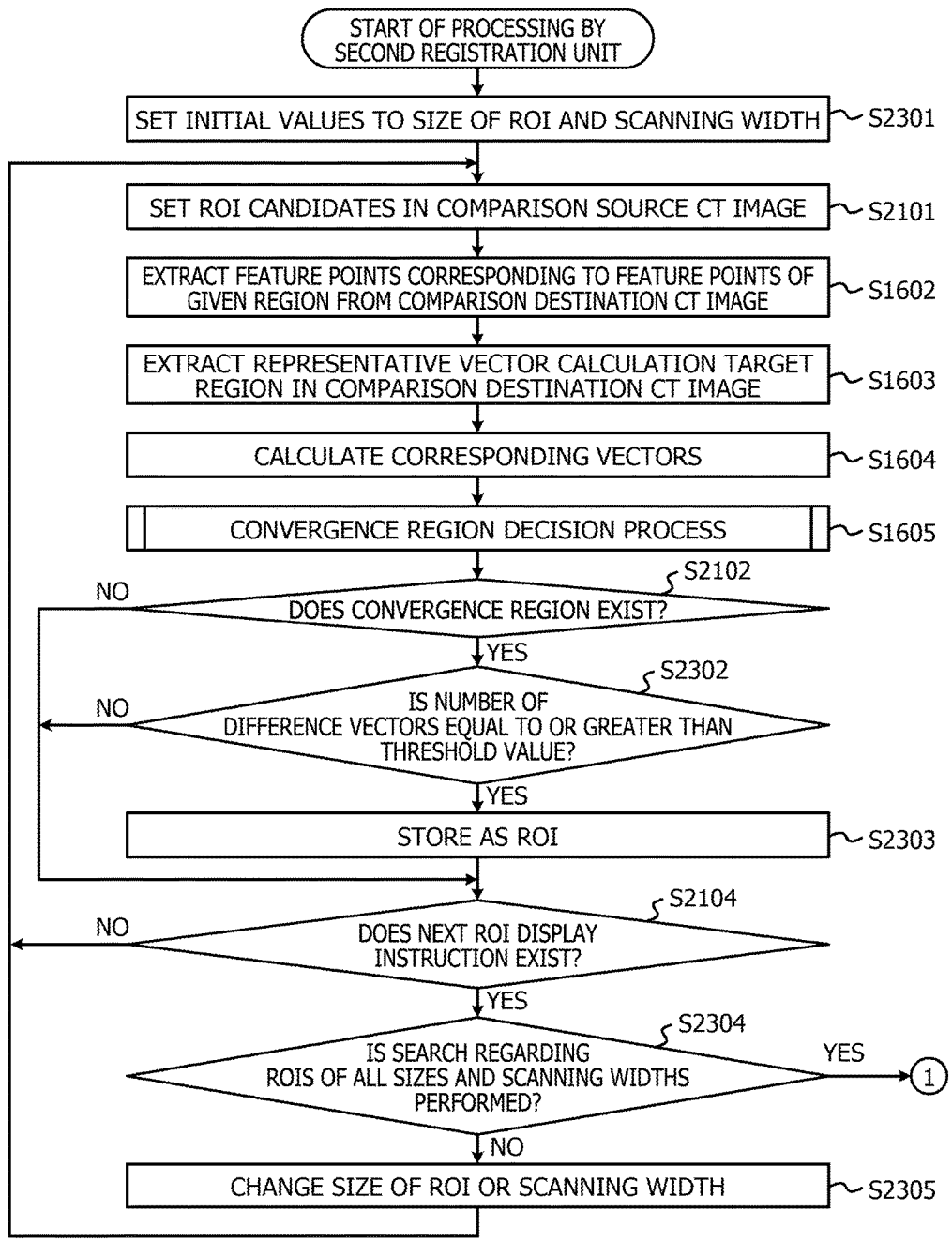
FIG. 23 is a third flow chart of a process executed by a second registration unit.
Figure 24:
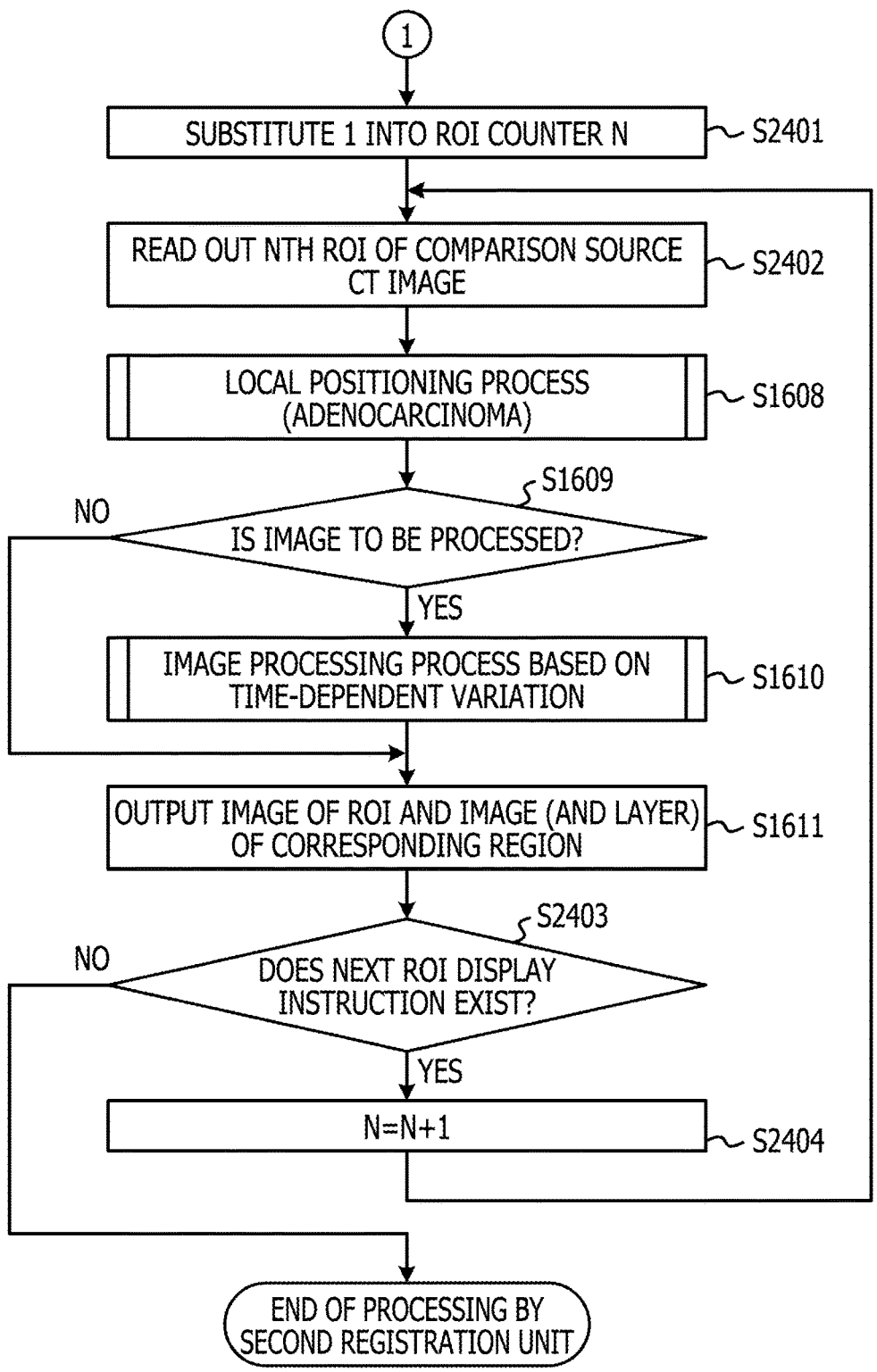
FIG. 24 is the third flow chart of a process executed by the second registration unit.

Now, a flow of processing by the second registration unit 142 in the third embodiment is described. FIGS. 23 and 24 are a third flow chart of processing executed by a second registration unit.

At step S2301, the region identification unit 1001 sets initial values for the size and the scanning width of an ROI candidate and reads out ROI candidates of the set size and scanning width from the auxiliary storage unit 204.

At step S2101, the region identification unit 1001 sets the ROI candidate read out at step S2301 to a scanning starting position of a comparison source CT image.

At steps S1602 to S1605, whether or not there exist a convergence region is decided on the basis of an image of a region specified by the ROI candidate at the position set at step S2101.

If the representative vector calculation unit 1004 decides at step S2102 that there exists no convergence region as a result of the processes at steps S1602 to S1605, then the processing advances to step S2104.

At step S2104, the region identification unit 1001 decides whether or not the ROI candidate exists at a terminal end position of the comparison source CT image (at the right lower end position of the comparison source CT image). If it is decided at step S2104 that the ROI candidate does not exist at the terminal end position, then the processing returns to step S2101.

In this case, the region identification unit 1001 sets the ROI candidate 2001 to a position displaced by a given scanning width (here, scanning width equal to the initial value therefor) on the comparison source CT image and then executes the processes at steps S1602 to S1605 again.

On the other hand, if it is decided that there exists a convergence region as a result of the processes at steps S1602 to S1605, then the representative vector calculation unit 1004 advances the processing from step S2102 to step S2302.

At step S2302, the region identification unit 1001 counts the number of difference vectors in a region specified by the position at which it is decided that there exists a convergence region, and decides whether or not the number of difference vectors is equal to or greater than a given threshold value.

If it is decided at step S2302 that the number of difference vectors is equal to or greater than the given threshold value, then the region identification unit 1001 decides the region specified by the ROI candidate at the position at present as a given region (ROI). Then, the processing advances to step S2303.

At step S2303, the region identification unit 1001 retains the region specified by the ROI candidate at the position at present as the given region (ROI).

On the other hand, if it is decided at step S2302 that the number of difference vectors is smaller than the given threshold value, then the region identification unit 1001 does not decide the region specified by the ROI candidate at the position at present as the given region (ROI). Then, the processing advances directly to step S2104.

It is to be noted that, since the process when it is decided at step S2104 that the ROI candidate is not at the terminal end position of the comparison source CT image is such as described above, description is given here of a case in which the ROI candidate is at the terminal end position of the comparison source CT image.

If it is decided at step S2104 that the ROI candidate is at the terminal end position of the comparison source CT image, then the processing advances to step S2304. At step S2304, the region identification unit 1001 decides whether or not the processes at steps S2101 to S2104 are executed with all scanning widths for all of the plurality of ROI candidates stored in the auxiliary storage unit 204.

If it is decided at step S2304 that there remains an ROI candidate for which the processes at steps S2101 to 2104 are not executed, then the processing advances to step S2305. Alternatively, if it is decided at step S2304 that there remains a scanning width that is not used in the processes, then the processing advances to step S2305.

At step S2305, the region identification unit 1001 reads out an ROI candidate for which the processes at steps S2101 to S2104 are not executed as yet from among the plurality of ROI candidates stored in the auxiliary storage unit 204, and then the processing returns to step S2101. Alternatively, the region identification unit 1001 sets a scanning width that is not used for the processes, and then returns the processing to step S2101.

In this case, the region identification unit 1001 sets the ROI candidate read out newly at step S2305 to the scanning starting position of the comparison source CT image. Alternatively, the region identification unit 1001 sets the ROI candidate read out at present to the scanning starting position of the comparison source CT image with the scanning width set at step S2305.

On the other hand, if it is decided at step S2304 that the region identification unit 1001 has executed the processes at steps S2101 to S2104 with all of the scanning widths for all of the plurality of ROI candidates stored in the auxiliary storage unit 204, then processing advances to step S2401.

At step S2401 of FIG. 24, the region identification unit 1001 substitutes 1 into an ROI counter N. It is to be noted that the ROI counter is a counter for counting the number of ROIs retained at step S2303 (regions decided each as given region (ROI)).

At step S2402, the region identification unit 1001 reads out an image of the Nth given region (ROI) from among the ROIs retained at step S2303. Here, the image in the first given region (ROI) is read out.

At step S1608, the representative vector calculation unit 1004 and the positioning unit 1005 perform a local positioning process of the adenocarcinoma. Further, if it is decided at step S1609 that the image processing process is to be performed, then the image processing process is performed at step S1610. Thereafter, the image in the Nth given region (ROI) and an image obtained by performing the image processing process for the image in the corresponding region 402 (including a translucent layer) are outputted to the display controller 143, whereafter the processing advances to step S2403.

Consequently, the display controller 143 causes an image of the Nth given region (ROI) 401 to be displayed in an enlarged scale on the comparison source CT image of the parallel display screen image 300, and causes an image (including the translucent layer) obtained by performing the image processing process for the image of the corresponding region 402 to be displayed in an enlarged scale on the comparison destination CT image.

At step S2403, the region identification unit 1001 decides whether or not a displaying instruction of a next ROI is received from the display controller 143. It is to be noted that, on the parallel display screen image 300, a health care worker can perform an operation for instructing to advance to a next ROI through the operation unit 207. Then, if an operation for instructing to advance to a next ROI is performed by a health care worker, then the display controller 143 notifies the region identification unit 1001 of the instruction.

If it is decided at step S2403 that a displaying instruction of a next ROI is received, then the processing advances to step S2404.

The region identification unit 1001 calculates the ROI counter N=N+1 at step S2404 and then returns the processing to step S2402, at which it reads out an image of the Nth given region (ROI). Here, an image of the second given region (ROI) is read out.

In this manner, at steps S2402 to S2404, a local positioning process and an image processing process are successively performed in accordance with an instruction from the health care worker on the basis of an image of the ROI retained at step S2303. Consequently, an image of the given region 401 and an image obtained by performing an image processing process for an image of the corresponding region 402 are successively displayed in an enlarged scale on the parallel display screen image 300.

On the other hand, if it is decided at step S2403 that a displaying instruction of a next ROI is not received, then the processing by the second registration unit 142 is ended.

As described above, the second registration unit 142 in the present embodiment performs scanning while the size and the scanning width of an ROI candidate are successively changed on the comparison source CT image. Further, the second registration unit 142 in the present embodiment determines a region specified at a position at which it is decided that a given condition is satisfied from among the positions at which it is decided that there exists a convergence region as a given region (ROI).

Consequently, the health care worker may no more perform a process for designating a tumor F on a comparison source CT image. Therefore, the load on the health care worker upon diagnosis can be reduced and, upon diagnosis, an optical ROI can be determined.

Fourth Embodiment

The image processing apparatus according to the first to third embodiments are described as apparatus that display an image (including a translucent layer) of a corresponding region for which an image processing process is performed by the second registration unit in an enlarged scale on a parallel display screen image.

In contrast, an image processing apparatus in the fourth embodiment changes, when an image (including a translucent layer) of a corresponding region for which an image processing process is performed by the second registration unit is to be displayed in an enlarged scale on a parallel display screen image, the display mode in response to an operation by a health care worker.

This is because, by an image processing process by the second registration unit, a plurality of layers are superposed on an image in a corresponding region and there is the possibility that the image of the corresponding region may become less easy to observe to the health care worker. In the following, the fourth embodiment is described principally of differences thereof from the first embodiment described hereinabove.

Figure 25:
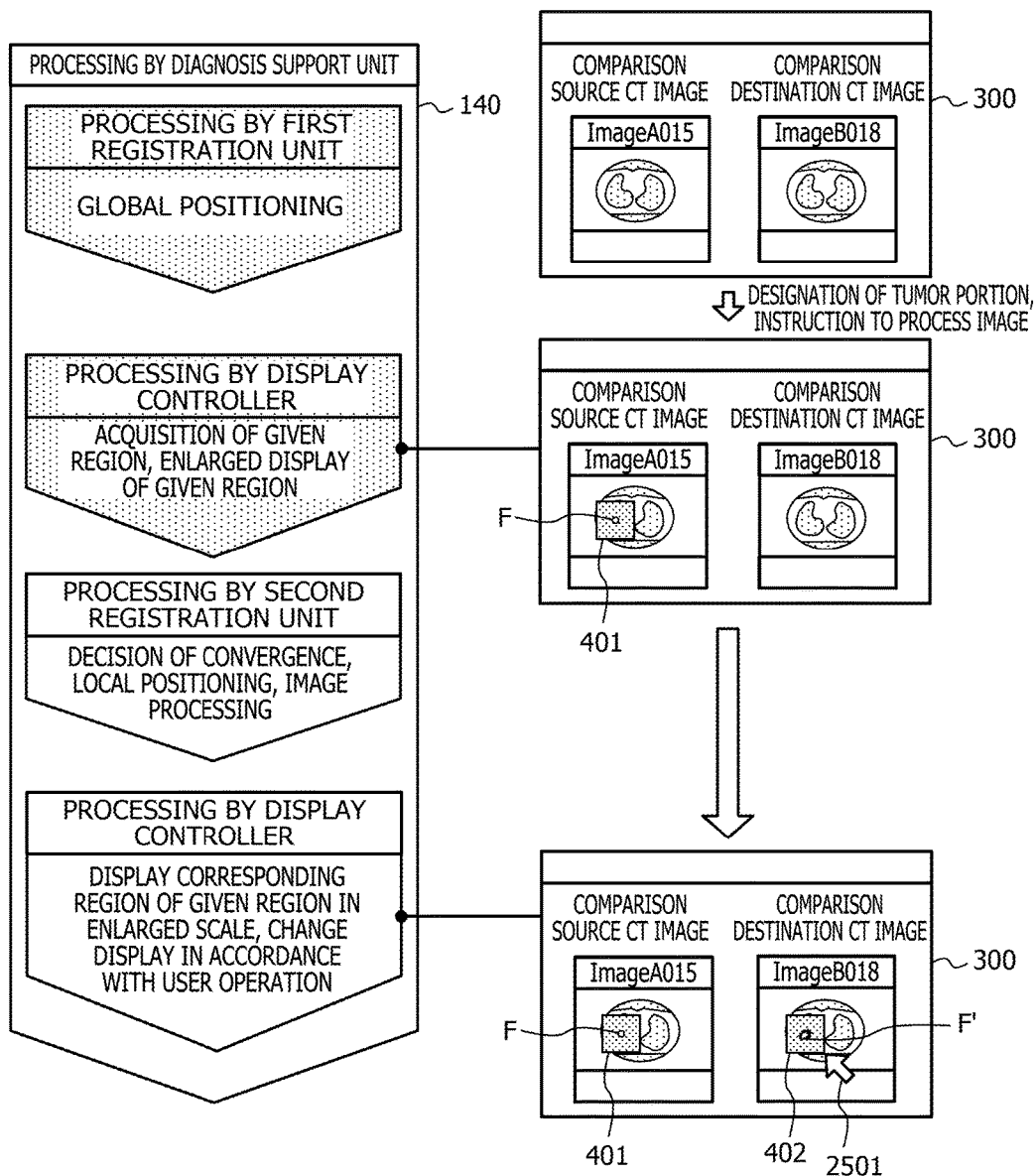
FIG. 25 is a third view illustrating a relationship among process contents of a diagnosis support unit of an image processing apparatus, operation contents of a health care worker, and display contents of a parallel display screen image.

FIG. 25 is a view illustrating a relationship among processing contents of a diagnosis support unit in an image processing apparatus, operation contents of a health care worker, and displaying contents of a parallel display screen image. FIG. 25 corresponds to FIG. 4 depicted in connection with the first embodiment described hereinabove (view illustrating processing contents and so forth later than global positioning).

As depicted in FIG. 25, if a health care worker designates a position of a tumor F on a displayed comparison source CT image, then an image of the given region (ROI) 401 is displayed in an enlarged scale on an enlarged display screen image on the comparison source CT image. Further, on the comparison destination CT image, an image for which an image processing process has been performed (including a translucent layer) is displayed in an enlarged scale on an enlarged display screen image on an image of the corresponding region 402 obtained by performing a local positioning process.

If a health care worker performs various operations for an image displayed in an enlarged scale on an enlarged screen image on a comparison destination CT image using a pointer 2501, then the display controller 143 changes the display mode of the image displayed in an enlarged scale on the enlarged display screen image on the comparison destination CT image in response to the various operations by the health care worker.

Figure 26:
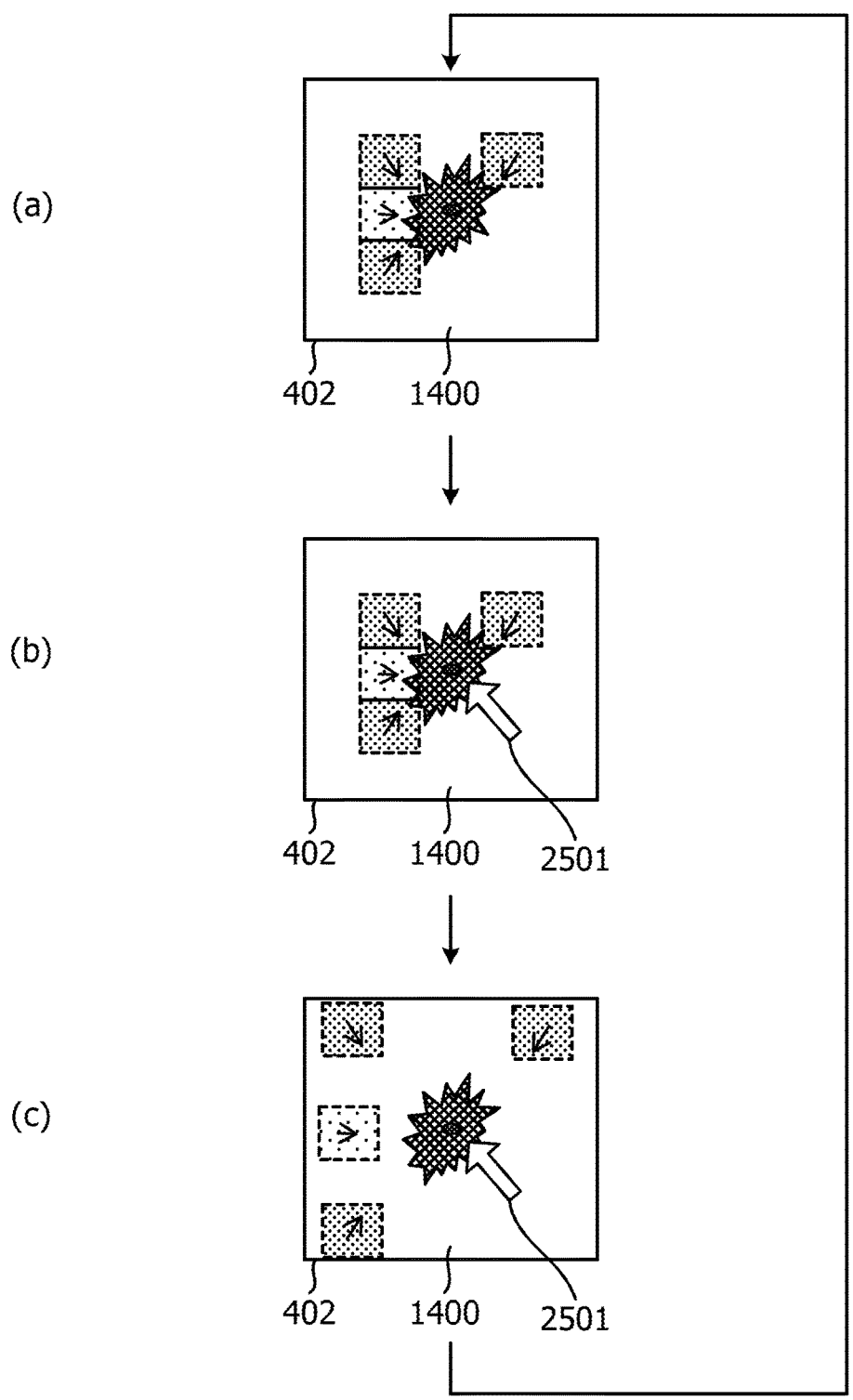
FIG. 26 depict views illustrating a manner in which a display mode of an enlarged display screen image is changed by a display controller.

FIG. 26 depict views illustrating a manner in which a display mode of an image of an enlarged display screen is changed by a display controller. FIG. 26A illustrates a manner in which a translucent layer on which difference vectors are displayed is superposed on an image 1400 of a corresponding region 402 and another translucent layer colored at partition groups 1102 at positions corresponding to the positions of the difference vectors is superposed further.

FIG. 26B illustrates a manner in which a health care worker moves a pointer 2501 toward the image 1400 of the corresponding region 402 on which the plurality of translucent layers are superposed.

FIG. 26C illustrates a manner in which, when the health care worker moves the pointer 2501 toward the center of the image 1400, on the translucent layer on which the difference vectors are displayed, the displayed difference vectors are retracted to the outside of a convergence region. Further, on the translucent layer colored at the partition groups 1102 at the positions corresponding to the positions of the difference vectors, the colored partition groups 1102 are retracted to the outside of the convergence region.

As depicted in FIG. 26C, the display controller 143 moves the displayed difference vectors such that the positions of the difference vectors are moved from the positions depicted in FIG. 26B to the outer side as viewed from a position at which the distal ends of the vectors are concentrated on the translucent layer. Further, the display controller 143 moves the colored partition groups 1102 to similar positions.

As a result, the partition groups 1102 on which the difference vectors are displayed and colored are not superposed on the convergence region of the image 1400 of the corresponding region 402, and therefore, it is facilitated for the health care worker to observe the convergence region. It is to be noted that, if the health care worker moves the pointer 2501 away from the image 1400, then the displayed difference vectors retracted to the outside of the convergence region are returned to the original positions as depicted in FIG. 26A. Further, the partition groups 1102 retracted to the outside of the convergence region are returned to the original positions.

It is to be noted that the display controller 143 may change, when to move displayed difference vectors to the outside of the convergence region on the translucent layer, the color of the difference vectors to a display color different from that of the difference vectors before the movement. Similarly, the display controller 143 may change, when to move the partition groups 1102 at the positions corresponding to the positions of the difference vectors to the outside of the convergence region on the translucent layer, the color such that the colors before and after the change are different from each other.

It is to be noted that, in the example of FIG. 26, a case is described in which displayed difference vectors (or colored partition groups 1102) are moved in response to the position of the pointer 2501. However, the movement of displayed difference vectors is not limited to this. For example, where the pointer 2501 is used to issue an instruction to display a further enlarged image, displayed difference vectors (or colored partition groups 1102) may be moved under a condition that the center of the enlarged display remains within the convergence region.

Figure 27:
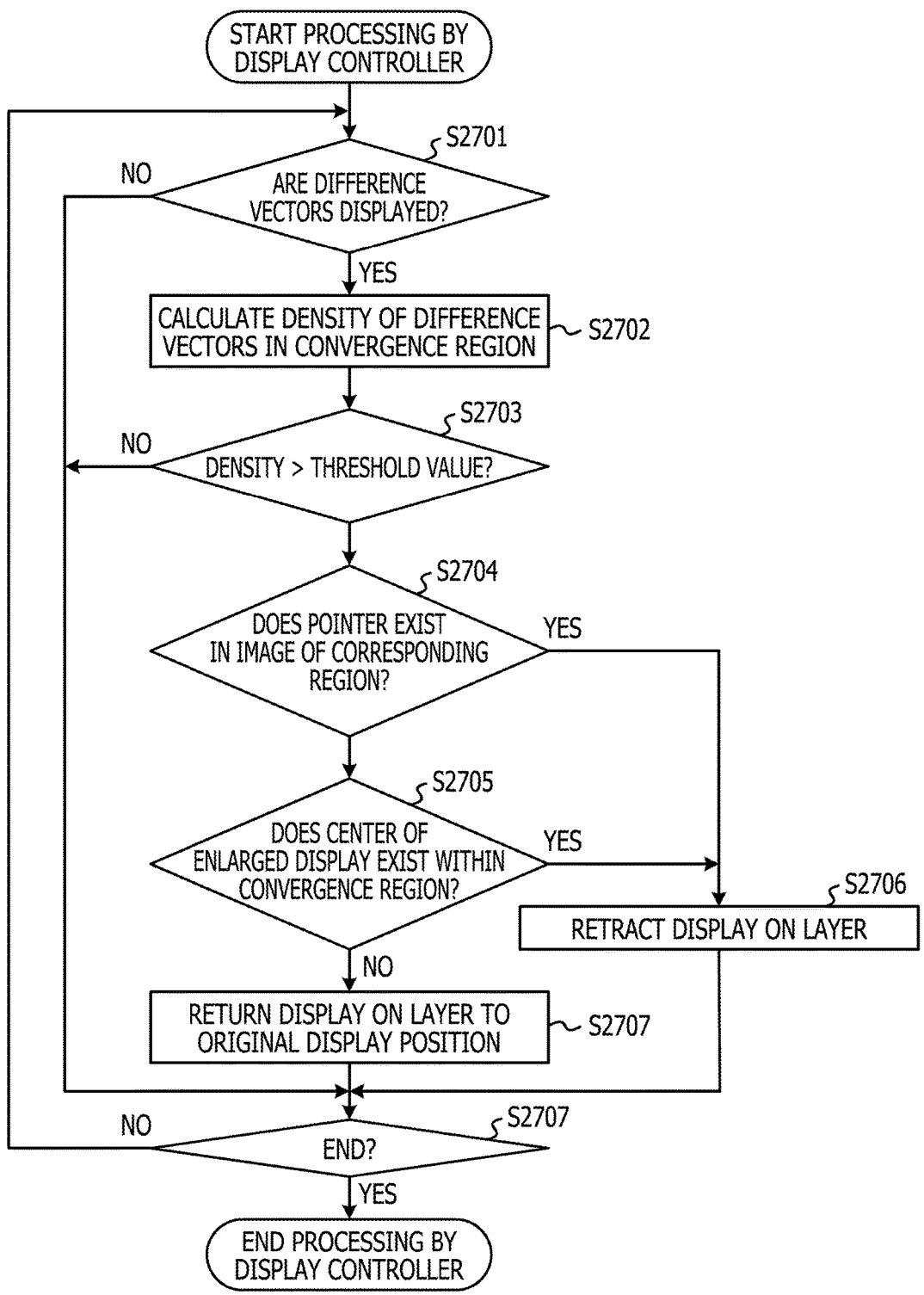
FIG. 27 is a flow chart of a process executed by a display controller.

Now, a flow of processing executed by the display controller 143 in the present embodiment is described. FIG. 27 is a flow chart of processing executed by a display controller.

At step S2701, the display controller 143 decides whether or not a layer on which difference vectors (or colored partition groups 1102) are displayed is superposed on an image 1400 of a corresponding region 402. If it is decided at step S2701 that a layer on which difference vectors (or colored partition groups 1102) are displayed is not superposed, then the processing advances to step S2708.

On the other hand, if it is decided at step S2701 that a layer on which difference vectors (or colored partition groups 1102) are displayed is superposed, then the processing advances to step S2702. At step S2702, the display controller 143 calculates a density of difference vectors in a convergence region on the image 1400 of the corresponding region 402. For example, the display controller 143 acquires a range of the convergence region calculated by the convergence region decision unit 1003 and a number of difference vectors included in the convergence region. Further, the display controller 143 calculates a density of the difference vectors in the convergence region ("overlapping ratio" calculated from the number of difference vectors superposed in the convergence region) on the basis of the acquired range of the convergence region and the acquired number of difference vectors.

At step S2703, the display controller 143 decides whether or not the density calculated at step S2702 is higher than a given threshold value (given ratio). If it is decided at step S2703 that the density is equal to lower than the given threshold value, then the processing advances to step S2708.

On the other hand, if it is decided at step S2703 that the density is higher than the given threshold value (namely, a number of difference vectors greater than a given ratio are placed in a region smaller than a given extent), then the processing advances to step S2704. At step S2704, the display controller 143 decides whether or not the pointer 2501 enters the image 1400 of the corresponding region 402.

If it is decided at step S2704 that the pointer 2501 enters the image 1400 of the corresponding region 402, then the processing advances to step S2706. At step S2706, the display controller 143 retracts the display (difference vectors or colored partition groups 1102) on the layer superposed on the image 1400 once to the outside of the convergence region.

On the other hand, if it is decided at step S2704 that the pointer 2501 does not enter the convergence region, then the processing advances to step S2705. At step S2705, the display controller 143 decides, when the health care worker instructs to perform display of the image 1400 in a further increased scale using the pointer 2501, whether or not the center of the enlarged display is within the convergence region.

If it is decided at step S2705 that the center of the enlarged display is within the convergence region, then the processing advances to step S2706. On the other hand, if it is decided at step S2705 that the center of the enlarged display is not within the convergence region, then the processing advances to step S2707.

At step S2707, if the display on the layer superposed on the image 1400 of the corresponding region 402 is retracted to the outside of the convergence region, the display controller 143 returns the display to its original display position. It is to be noted that the display controller 143 maintains the current display position if the display on the layer superposed on the image 1400 is not retracted to the outside of the convergence display (in the case the display on the original display position).

At step S2708, the display controller 143 decides whether or not the processing being executed is to be ended. It is to be noted that the case in which the process being executed is to be ended is a case in which the display of the image 1400 of the corresponding region 402 displayed at present is ended. The case in which the display of the image 1400 of the corresponding region 402 being displayed at present is, for example, a case in which a given region different from the given region displayed at present is designated, another case in which a comparison source CT image different from the comparison source CT image being displayed at present is displayed or a like case.

If it is decided at step S2708 that the process being executed is not to be ended, then the processing returns to step S2701. On the other hand, if it is decided at step S2708 that the processing being executed is to be ended, then the processing is ended.

As described above, in the display controller 143 in the present embodiment, a display on a layer superposed on an image of a corresponding region is moved to the outside of a convergence region in response to a pointer operation by a health care worker. Consequently, the health care worker can reduce difficulty in observing a convergence region (portion to be diagnosed) on an image of a corresponding region.

Fifth Embodiment

In the first embodiment described hereinabove, the image processor 1006 visualizes a tendency of a change of a tissue based on a change of a tumor on the basis of a calculated distribution of difference vectors (number of difference vectors per unit area). However, the method for the visualization of a tendency of a change of a tissue is not limited to this. For example, a speed of change of a tissue may be calculated and visualized on the basis of the magnitude and the elapsed time of the calculated difference vectors.

Further, in the third embodiment described hereinabove, the second registration unit 142 determines a region in which the number of difference vectors is equal to or greater than a given threshold value from among regions in which it is decided that there exists a convergence region as an ROI. However, the determination method of an ROI is not limited to this. Any other determination method may be used if it can determine a region in which the degree of convergence of a tissue is high is an ROI.

Further, in the third embodiment described above, an image processing process is executed after all ROIs are determined on a comparison source CT image. However, an image processing process may otherwise be executed every time an ROI is determined.

Further, in the first to fourth embodiments described hereinabove, an image of a given region (ROI) is displayed in an enlarged scale on an enlarged display screen image. However, an image of a given region (ROI) may be displayed in an enlarged scale on a comparison source CT image like a loupe view.

Further, in the first to fourth embodiments described hereinabove, an instruction for image processing is accepted after global positioning is completed. However, an instruction for image processing may be accepted otherwise after an image of a corresponding image is displayed.

Further, in the first to fourth embodiments described hereinabove, a CT image is displayed. However, the embodiments disclosed herein may be applied also to a case in which a medical image other than a CT image (for example, a magnetic resonance imaging (MRI) image) is displayed.

It is to be noted that the embodiments disclosed herein is not limited to the configurations described hereinabove in connection with the embodiments and the configurations may have some other elements combined therewith. The configurations of the embodiments can be modified in various manners without departing from the spirit and scope of the present embodiments and can be applied appropriately in accordance with an application form thereof.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A non-transitory computer readable storage medium storing a program that causes a computer to execute a process comprising:
    obtaining a first image of a chest and a second image of the chest scanned after the first image;
    specifying a plurality of difference vectors indicating a changes of a plurality of positions in a lung between the first image and the second image;
    determining whether a change in the lung occurs, the change being a change indicated by specified difference vectors, in the plurality of difference vectors, toward a specified position in the lung;
    transforming the second image to adjust the plurality of positions in the second image to the plurality of positions in the first image based on the plurality of difference vectors far from the specified position by a predetermined distance or more; and
    outputting the transformed second image on a display device.

2. The non-transitory computer readable storage medium according to claim 1, wherein
    an area corresponding to the change in the lung is displayed on the display device.

3. The non-transitory computer readable storage medium according to claim 2, wherein
    the specified position is displayed on the display device in a different manner from other parts of the lung.

4. The non-transitory computer readable storage medium according to claim 1, wherein
    the plurality of difference vectors toward the specified position is displayed so as to be superposed on the transformed second image.

5. The non-transitory computer readable storage medium according to claim 4, wherein
    the plurality of difference far from the specified position by the predetermined distance or more is vectors indicating the change of the lung that is caused by breathing and a heart beating, is excluded from the specified vectors.

6. The non-transitory computer readable storage medium according to claim 1, wherein
    the change in the lung indicates that alveoli in the lung are collapsed by an adenocarcinoma.

7. An apparatus for image processing, the apparatus comprising:
    a memory; and
    a processor coupled to the memory and configured to:
        obtaining a first image of a chest and a second image of the chest scanned after the first image;
        specifying a plurality of difference vectors indicating a changes of a plurality of positions in a lung between the first image and the second image;
        determine whether a change in the lung occurs, the change being a change indicated by specified difference vectors, in the plurality of difference vectors, toward a specified position in the lung;
        transform the second image to adjust the plurality of positions in the second image to the plurality of positions in the first image based on the plurality of difference vectors far from the specified position by a predetermined distance or more; and
        output the transformed second image on a display device.

8. A method for image processing, the method comprising:
    obtaining a first image of a chest and a second image of the chest scanned after the first image;
    specifying a plurality of difference vectors indicating a changes of a plurality of positions in a lung between the first image and the second image;
    determining whether a change in the lung occurs, the change being a change indicated by specified difference vectors, in the plurality of difference vectors, toward a specified position in the lung;
    transforming the second image to adjust the plurality of positions in the second image to the plurality of positions in the first image based on the plurality of difference vectors far from the specified position by a predetermined distance or more; and
    outputting the transformed second image on a display device.

* * * * *